US011109969B2

(12) United States Patent
Vidlund et al.

(10) Patent No.: US 11,109,969 B2
(45) Date of Patent: Sep. 7, 2021

(54) GUIDEWIRE DELIVERY OF TRANSCATHETER HEART VALVE

(71) Applicant: VDyne, Inc., Maple Grove, MN (US)

(72) Inventors: Robert Vidlund, Forest Lake, MN (US); Mark Christianson, Plymouth, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 16/448,108

(22) Filed: Jun. 21, 2019

(65) Prior Publication Data
US 2020/0121458 A1 Apr. 23, 2020

Related U.S. Application Data

(60) Provisional application No. 62/749,121, filed on Oct. 22, 2018.

(51) Int. Cl.
*A61F 2/24* (2006.01)
(52) U.S. Cl.
CPC .......... *A61F 2/2436* (2013.01); *A61F 2/2418* (2013.01); *A61F 2/2466* (2013.01); *A61F 2/2433* (2013.01); *A61F 2210/0014* (2013.01)
(58) Field of Classification Search
CPC .... A61F 2/2427; A61F 2/2436; A61F 2/2439; A61F 2/24; A61F 2/2418; A61F 2/954; A61F 2/962; A61F 2/966; A61F 2/95; A61F 2002/9528; A61F 2002/9534; A61F 2002/9665; A61F 2002/9511; A61F 2002/9505
See application file for complete search history.

(56) References Cited

U.S. PATENT DOCUMENTS

| | | | |
|---|---|---|---|
| 5,397,351 A | 3/1995 | Pavcnik et al. | |
| 5,509,428 A | 4/1996 | Dunlop | |
| 6,006,134 A | 12/1999 | Hill et al. | |
| 6,197,013 B1 | 3/2001 | Reed et al. | |
| 6,290,719 B1 | 9/2001 | Garberoglio | |
| 6,449,507 B1 | 9/2002 | Hill et al. | |
| 6,532,388 B1 | 3/2003 | Hill et al. | |
| 6,582,467 B1 | 6/2003 | Teitelbaum et al. | |
| 6,628,987 B1 | 9/2003 | Hill et al. | |
| 6,718,208 B2 | 4/2004 | Hill et al. | |

(Continued)

FOREIGN PATENT DOCUMENTS

| | | |
|---|---|---|
| AU | 2006203686 B2 | 11/2008 |
| AU | 2009219415 A1 | 9/2009 |

(Continued)

OTHER PUBLICATIONS

Office Action for U.S. Appl. No. 16/435,687, dated Aug. 7, 2019, 19 pages.

(Continued)

*Primary Examiner* — Elizabeth Houston
*Assistant Examiner* — Lindsey Bachman

(57) ABSTRACT

The invention relates to delivery system for deployment of a prosthetic valve, having a hypotube sheathed guidewire assembly having an outer sheath and an inner guidewire shaft that pushes against a guidewire collar on a tension arm of a compressed transcatheter valve to deliver the valve and position the valve to the RVOT or other location in the body.

10 Claims, 18 Drawing Sheets

(56) References Cited

U.S. PATENT DOCUMENTS

| | | |
|---|---|---|
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,074,189 B1 | 7/2006 | Montegrande |
| 7,125,418 B2 | 10/2006 | Duran et al. |
| 7,176,660 B2 | 2/2007 | Cartiedge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,374,571 B2 | 5/2008 | Pease et al. |
| 7,449,027 B2 | 11/2008 | Hunt et al. |
| 7,717,952 B2 | 5/2010 | Case et al. |
| 7,749,245 B2 | 7/2010 | Cohn et al. |
| 7,753,949 B2 | 7/2010 | Lamphere et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest et al. |
| 9,011,524 B2 | 4/2015 | Eberhardt |
| 9,017,399 B2 | 4/2015 | Gross et al. |
| 9,050,188 B2 | 6/2015 | Schweich, Jr. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,510,941 B2 | 12/2016 | Bishop et al. |
| 9,554,902 B2 | 1/2017 | Braido |
| 9,579,196 B2 | 2/2017 | Morriss et al. |
| 9,579,200 B2 | 2/2017 | Lederman et al. |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 | 2/2018 | Costello |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman |
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |
| 10,080,653 B2 | 9/2018 | Conklin et al. |
| 10,085,835 B2 | 10/2018 | Thambar et al. |
| 10,105,224 B2 | 10/2018 | Buchbinder |
| 10,117,741 B2 | 11/2018 | Schweich, Jr. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 2003/0040772 A1 | 2/2003 | Hyodoh et al. |

(56) References Cited

U.S. PATENT DOCUMENTS

| | | |
|---|---|---|
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0088047 A1 | 5/2004 | Spence et al. |
| 2004/0116996 A1* | 6/2004 | Freitag ............... A61F 2/88 623/1.11 |
| 2004/0199209 A1 | 10/2004 | Hill et al. |
| 2005/0010246 A1 | 1/2005 | Streeter et al. |
| 2005/0107811 A1 | 5/2005 | Starksen et al. |
| 2005/0137686 A1* | 6/2005 | Salahieh ............. A61F 2/2418 623/2.11 |
| 2006/0015167 A1 | 1/2006 | Armstrong |
| 2006/0190075 A1* | 8/2006 | Jordan ............... A61F 2/90 623/1.23 |
| 2006/0195180 A1 | 8/2006 | Kheradvar et al. |
| 2006/0271098 A1 | 11/2006 | Peacock, III |
| 2006/0276887 A1* | 12/2006 | Brady ................ A61F 2/90 623/1.53 |
| 2007/0016286 A1 | 1/2007 | Herrmann |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1* | 5/2007 | Perouse ............... A61F 2/07 623/1.11 |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0071287 A1* | 3/2008 | Goto ................ A61B 17/221 606/108 |
| 2008/0132999 A1 | 6/2008 | Mericle et al. |
| 2008/0140181 A1* | 6/2008 | Reynolds ............. A61F 2/91 623/1.15 |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1* | 10/2008 | Jordan ............... A61F 2/95 623/1.11 |
| 2008/0262609 A1 | 10/2008 | Gross et al. |
| 2008/0275550 A1 | 11/2008 | Kheradvar et al. |
| 2009/0005863 A1* | 1/2009 | Goetz ............... A61F 2/2418 623/2.18 |
| 2009/0094189 A1 | 4/2009 | Stephens |
| 2009/0192586 A1 | 7/2009 | Tabor et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1* | 2/2010 | Zukowski ............ A61F 2/954 623/1.11 |
| 2010/0049313 A1* | 2/2010 | Alon ............... A61F 2/2418 623/2.11 |
| 2010/0121434 A1* | 5/2010 | Paul .................. A61F 2/90 623/2.11 |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter |
| 2010/0179584 A1 | 7/2010 | Carpenter |
| 2010/0179647 A1 | 7/2010 | Carpenter |
| 2010/0280591 A1* | 11/2010 | Shin .................. A61F 2/90 623/1.15 |
| 2010/0305685 A1 | 12/2010 | Millwee et al. |
| 2011/0029071 A1 | 2/2011 | Zlotnick et al. |
| 2011/0071613 A1* | 3/2011 | Wood ................ A61F 2/88 623/1.11 |
| 2011/0098804 A1 | 4/2011 | Yeung et al. |
| 2011/0125145 A1 | 5/2011 | Mody, I et al. |
| 2011/0160836 A1* | 6/2011 | Behan ............... A61F 2/06 623/1.11 |
| 2011/0172764 A1 | 7/2011 | Badhwar |
| 2011/0224785 A1 | 9/2011 | Hacohen et al. |
| 2011/0245911 A1* | 10/2011 | Quill .................. A61F 2/2418 623/1.26 |
| 2011/0245917 A1 | 10/2011 | Savage |
| 2011/0251675 A1 | 10/2011 | Dwork |
| 2011/0257721 A1 | 10/2011 | Tabor |
| 2011/0264191 A1* | 10/2011 | Rothstein ............. A61F 2/2418 623/1.11 |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMONTELLE |
| 2012/0203336 A1* | 8/2012 | Annest ............... A61F 2/2436 623/2.36 |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1* | 12/2012 | McHugo ............ A61F 2/90 623/1.15 |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1* | 6/2013 | Cartledge ............ A61F 2/93 623/1.15 |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. |
| 2013/0297010 A1 | 11/2013 | Bishop et al. |
| 2013/0331929 A1 | 12/2013 | Mitra et al. |
| 2014/0000112 A1 | 1/2014 | Braido |
| 2014/0005540 A1 | 1/2014 | Merhi |
| 2014/0005768 A1 | 1/2014 | Thomas |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1* | 9/2014 | Roeder ............... A61F 2/966 623/1.11 |
| 2014/0277388 A1 | 9/2014 | Skemp |

(56) References Cited

U.S. PATENT DOCUMENTS

| | | |
|---|---|---|
| 2014/0277408 A1 | 9/2014 | Folan |
| 2014/0296962 A1* | 10/2014 | Cartledge ............... A61F 2/844 623/1.12 |
| 2014/0296969 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0371789 A1 | 12/2014 | Hariton et al. |
| 2014/0379076 A1 | 12/2014 | Vidlund |
| 2015/0005808 A1 | 1/2015 | Chouinard et al. |
| 2015/0005874 A1 | 1/2015 | Vidlund et al. |
| 2015/0039081 A1* | 2/2015 | Costello ............... A61F 2/2418 623/2.11 |
| 2015/0045880 A1 | 2/2015 | Hacohen |
| 2015/0051687 A1 | 2/2015 | Dickerhoff |
| 2015/0094802 A1 | 4/2015 | Buchbinder |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1* | 10/2015 | Hingston ............... A61F 2/95 623/23.7 |
| 2015/0282931 A1* | 10/2015 | Brunnett ............... A61F 2/2412 623/2.11 |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell |
| 2015/0351904 A1 | 12/2015 | Cooper |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1* | 7/2016 | Hacohen ............... A61F 2/2403 |
| 2016/0220367 A1 | 8/2016 | Barrett |
| 2016/0220372 A1 | 8/2016 | Medema et al. |
| 2016/0220734 A1 | 8/2016 | Dyamenahalli |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324639 A1 | 11/2016 | Nguyen et al. |
| 2016/0331534 A1 | 11/2016 | Buchbinder |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper |
| 2017/0071733 A1* | 3/2017 | Ghione ............... A61F 2/2412 |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |
| 2017/0112620 A1 | 4/2017 | Curley et al. |
| 2017/0128208 A1 | 5/2017 | Christianson |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0181851 A1 | 6/2017 | Annest |
| 2017/0189177 A1 | 7/2017 | Schweich, Jr. |
| 2017/0196690 A1 | 7/2017 | Racchini et al. |
| 2017/0209266 A1 | 7/2017 | Lane et al. |
| 2017/0209268 A1* | 7/2017 | Cunningham ........ A61F 2/2418 |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini |
| 2017/0281337 A1 | 10/2017 | Campbell |
| 2017/0281341 A1* | 10/2017 | Lim ............... A61F 2/2418 |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1* | 11/2017 | Stangenes ........ A61B 17/00234 |
| 2017/0348099 A1 | 12/2017 | Mendelson |
| 2017/0348100 A1 | 12/2017 | Lane et al. |
| 2017/0360558 A1 | 12/2017 | Ma |
| 2017/0360561 A1 | 12/2017 | Bell et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |

(56) References Cited

U.S. PATENT DOCUMENTS

| | | |
|---|---|---|
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | Mcloughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1* | 6/2018 | Maimon ............ A61F 2/2418 |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk |
| 2018/0263767 A1 | 9/2018 | Chau et al. |
| 2018/0263773 A1* | 9/2018 | Poppe .................. A61F 2/966 |
| 2018/0280174 A1 | 10/2018 | Dwork |
| 2018/0289474 A1 | 10/2018 | Rajagopal |
| 2018/0289475 A1 | 10/2018 | Chung et al. |
| 2018/0289485 A1 | 10/2018 | Rajagopal et al. |
| 2018/0296335 A1 | 10/2018 | Miyashiro |
| 2018/0296337 A1 | 10/2018 | Duhay et al. |
| 2018/0303488 A1 | 10/2018 | Hill |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0338832 A1 | 11/2018 | Ganesan et al. |
| 2018/0344456 A1* | 12/2018 | Barash ................ A61F 2/2418 |
| 2018/0353293 A1 | 12/2018 | Colavito et al. |
| 2018/0353295 A1 | 12/2018 | Cooper |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper |
| 2019/0015188 A1 | 1/2019 | Eigler et al. |
| 2019/0021834 A1 | 1/2019 | Nir et al. |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1* | 2/2019 | Cohen .................. A61F 2/243 |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno, V et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman |
| 2019/0254816 A1 | 8/2019 | Anderson et al. |
| 2019/0262118 A1 | 8/2019 | Eigler et al. |
| 2019/0262129 A1 | 8/2019 | Cooper |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0388219 A1 | 12/2019 | Lane et al. |
| 2020/0121452 A1 | 4/2020 | Saikrishnan et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |

(56) References Cited

FOREIGN PATENT DOCUMENTS

| | | |
|---|---|---|
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |

(56) References Cited

FOREIGN PATENT DOCUMENTS

| | | | |
|---|---|---|---|
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |

(56) References Cited

FOREIGN PATENT DOCUMENTS

| | | | |
|---|---|---|---|
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |

(56) References Cited

FOREIGN PATENT DOCUMENTS

| | | |
|---|---|---|
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019086958 A1 | 5/2019 |
| WO | WO-2019081689 A1 | 5/2019 |
| WO | WO-2019081985 A2 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

International Search Report and Written Opinion for International Application No. PCT/US2019/051615, dated Mar. 2, 2020, 14 pages.

International Search Report and Written Opinion for International Application No. PCT/US2019/051957, dated Apr. 30, 2020, 16 pages.

Office Action for U.S. Appl. No. 16/155,890, dated Feb. 8, 2019, 13 pages.

Office Action for U.S. Appl. No. 16/163,577, dated Mar. 8, 2021, 10 pages.

Office Action for U.S. Appl. No. 16/455,417, dated Sep. 23, 2019, 11 pages.

International Search Report and Written Opinion for International Application No. PCT/US2019/067010, dated Mar. 10, 2020, 17 pages.

Office Action for U.S. Appl. No. 16/455,740, dated Jul. 24, 2020, 7 pages.

International Search Report and Written Opinion for International Application No. PCT/US2020/015231, dated Apr. 23, 2020, 10 pages.

International Search Report and Written Opinion for International Application No. PCT/US2020/021300, dated Oct. 7, 2020, 6 pages.

International Search Report and Written Opinion for International Application No. PCT/US2020/031390, dated Aug. 3, 2020, 10 pages.

International Search Report and Written Opinion for International Application No. PCT/US2020/013240, dated Jun. 3, 2020, 7 pages.

International Search Report and Written Opinion for International Application No. PCT/US2020/022828, dated May 19, 2020, 12 pages.

Office Action for U.S. Appl. No. 17/154,227, dated Mar. 29, 2021, 6 pages.

Office Action for U.S. Appl. No. 16/442,504, dated Jan. 14, 2020, 11 pages.

Office Action for U.S. Appl. No. 16/445,210, dated Jan. 28, 2021, 7 pages.

International Search Report and Written Opinion for International Application No. PCT/US2020/045195, dated Jan. 8, 2021, 18 pages.

International Search Report and Written Opinion for International Application No. PCT/US2020/047162, dated Dec. 30, 2020, 9 pages.

Office Action for U.S. Appl. No. 17/193,936, dated May 27, 2021, 6 pages.

International Search Report and Written Opinion for International Application No. PCT/US2019/028822, dated Oct. 24, 2019, 14 pages.

Office Action for U.S. Appl. No. 17/167,983, dated Apr. 13, 2021, 20 pages.

Office Action for U.S. Appl. No. 17/154,438, dated May 3, 2021, 16 pages.

International Search Report and Written Opinion for International Application No. PCT/US2021/013570, dated Apr. 1, 2021, 9 pages.

Office Action for U.S. Appl. No. 17/154,227, dated Jun. 18, 2021, 8 pages.

* cited by examiner

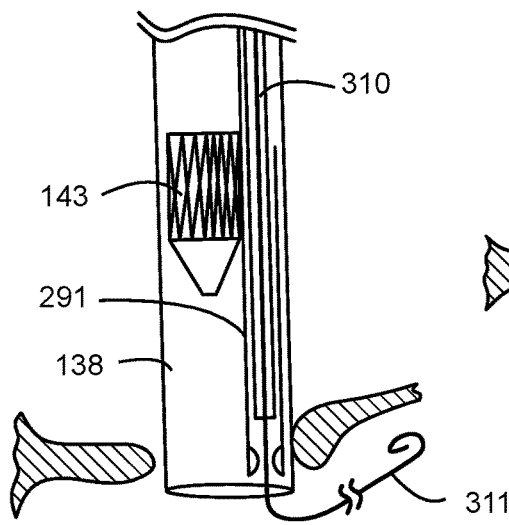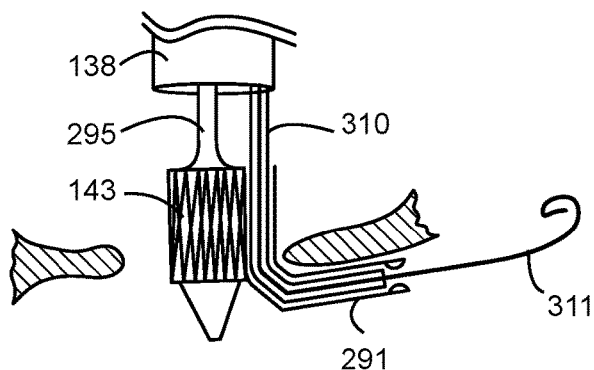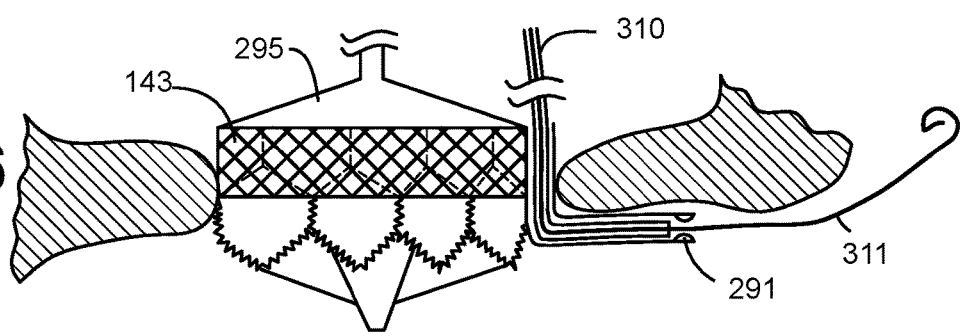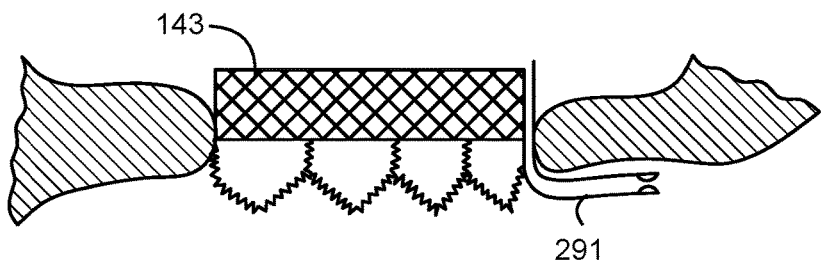

GUIDEWIRE DELIVERY OF TRANSCATHETER HEART VALVE

CROSS-REFERENCE TO RELATED APPLICATIONS

Provided by Application Data Sheet per USPTO rules.

STATEMENT REGARDING FEDERALLY SPONSORED R&D

Provided by Application Data Sheet per with USPTO rules.

NAMES OF PARTIES TO JOINT RESEARCH AGREEMENT

Provided by Application Data Sheet per with USPTO rules.

REFERENCE TO SEQUENCE LISTING

Provided by Application Data Sheet per USPTO rules.

STATEMENT RE PRIOR DISCLOSURES

Provided by Application Data Sheet per USPTO rules.

BACKGROUND OF THE INVENTION

Field of the Invention

The invention relates to delivery system for deployment of a prosthetic valve, having a hypotube sheathed guidewire assembly having an outer sheath and an inner guidewire shaft that pushes against a guidewire collar on a tension arm of a compressed transcatheter valve to deliver the valve and position the valve to the tricuspid valve or mitral valve location in the body.

DESCRIPTION OF THE RELATED ART

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting disc technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

Accordingly, the present invention is directed to a delivery system for deployment of a prosthetic valve, comprising:

(i) a hypotube sheathed guidewire assembly having an outer sheath and an inner guidewire shaft;

(ii) a transcatheter prosthetic valve having a tubular frame with a flow control component mounted within the tubular frame and configured to permit blood flow in a first direction through an inflow end of the valve and block blood flow in a second direction, opposite the first direction, through an outflow end of the valve, said tubular frame having a tension arm extending from a distal side of the tubular frame, the tension arm comprised of wire loop or wire frame, integrated frame section, or stent, extending from about 10-40 mm away from the tubular frame, said tension arm having a guidewire collar element attached the tension arm, wherein the guidewire collar element is sized and configured with a guidewire aperture to allow the inner guidewire shaft of the hypotube sheathed guidewire assembly to pass through the guide aperture, and to block passage of the outer sheath of the guidewire assembly through the guidewire aperture;

(iii) a delivery catheter, the delivery catheter comprising an elongated tube with a central lumen, the lumen having a diameter from about 7 to 11 mm; wherein the valve is compressible to a compressed configuration for introduction into the body using the delivery catheter for implanting at a desired location in the body, wherein the valve has a height of about 5-60 mm and a diameter of about 25-80 mm.

In another preferred embodiment of the present invention, there is provided a delivery system wherein the compressed configuration of the valve is co-axial with the first direction.

In another preferred embodiment of the present invention, there is provided a delivery system wherein the valve is a balloon-inflated valve.

In another preferred embodiment of the present invention, there is provided a delivery system, wherein the valve is a self-expanding valve.

In another preferred embodiment of the present invention, there is provided a delivery system, wherein the compressed configuration of the valve is orthogonal to the axis of the first direction, wherein said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter.

In another preferred embodiment of the present invention, there is provided a method for delivering a valve, comprising the steps:

advancing a guidewire to a desired location within a body, said guidewire having an outer sheath and an inner shaft;

advancing a delivery catheter over the guidewire to the desired location;

mounting a valve capsule onto a proximal end of the guidewire, said valve capsule containing a compressed valve having a threaded guidewire collar, the guidewire extending through the threaded guidewire collar, the threaded guidewire collar having an aperture sized to permit the inner shaft to extend through the aperture and to block the outer sheath from extending through the aperture;

loading the valve capsule into a proximal end of the delivery catheter;

advancing the compressed valve from the valve capsule into and through a lumen of the delivery catheter to the desired location by advancing the outer sheath over the inner shaft, to deploy the valve at the desired location.

In another preferred embodiment of the present invention, there is provided a delivery method wherein the compressed configuration of the valve is co-axial with the first direction.

In another preferred embodiment of the present invention, there is provided a delivery method wherein the valve is a balloon-inflated valve.

In another preferred embodiment of the present invention, there is provided a delivery method wherein the valve is a self-expanding valve.

In another preferred embodiment of the present invention, there is provided a delivery method wherein the compressed configuration of the valve is orthogonal to the axis of the first direction, wherein said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter.

In another preferred embodiment of the present invention, there is provided a delivery system for deployment of a prosthetic valve into a valve frame, comprising:

(i) a hypotube sheathed guidewire assembly having an outer sheath and an inner guidewire shaft;

(ii) a transcatheter prosthetic valve frame for a valve in frame prosthesis system, comprising: a tubular frame having a central lumen defined by an inner circumferential surface of the tubular frame, and a tension arm extending from a distal side of the tubular frame, the tension arm comprised of wire loop or wire frame, integrated frame section, or stent, extending from about 10-40 mm away from the tubular frame, said tension arm having a guidewire collar element attached the tension arm, wherein the guidewire collar element is sized and configured with a guidewire aperture to allow the inner guidewire shaft of the hypotube sheathed guidewire assembly to pass through the guide aperture, and to block passage of the outer sheath of the guidewire assembly through the guidewire aperture;

(iii) a delivery catheter, the delivery catheter comprising an elongated tube with a central lumen, the lumen having a diameter from about 7 to 11 mm; wherein the tubular frame is compressible to a compressed configuration for introduction into the body using a delivery catheter for implanting at a desired location in the body, wherein the tubular frame has a height of about 5-60 mm and a diameter of about 25-80 mm.

In another preferred embodiment of the present invention, there is provided a frame delivery system wherein the compressed configuration of the valve is co-axial with the first direction.

In another preferred embodiment of the present invention, there is provided a frame delivery system wherein the valve is a balloon-inflated valve.

In another preferred embodiment of the present invention, there is provided a frame delivery system wherein the valve is a self-expanding valve.

In another preferred embodiment of the present invention, there is provided a frame delivery system wherein the compressed configuration of the valve is orthogonal to the axis of the first direction, wherein said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter.

BRIEF DESCRIPTION OF THE DRAWING FIGURES

FIG. 1 is an illustration of a side or plan transparent view of a delivery catheter loaded with an orthogonal valve having a tension arm with a guidewire collar element and a guidewire extending through the guidewire collar with a guidewire sheath pushing against the guidewire collar element. Inset shows a non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

FIG. 5 shows an 0.035 guidewire with hypotube sheath delivered to the right ventricular outflow tract (RVOT).

FIG. 6 shows a 34 Fr delivery catheter being advanced over the guidewire to and through the native tricuspid annulus to the right ventricle.

Figure 7:
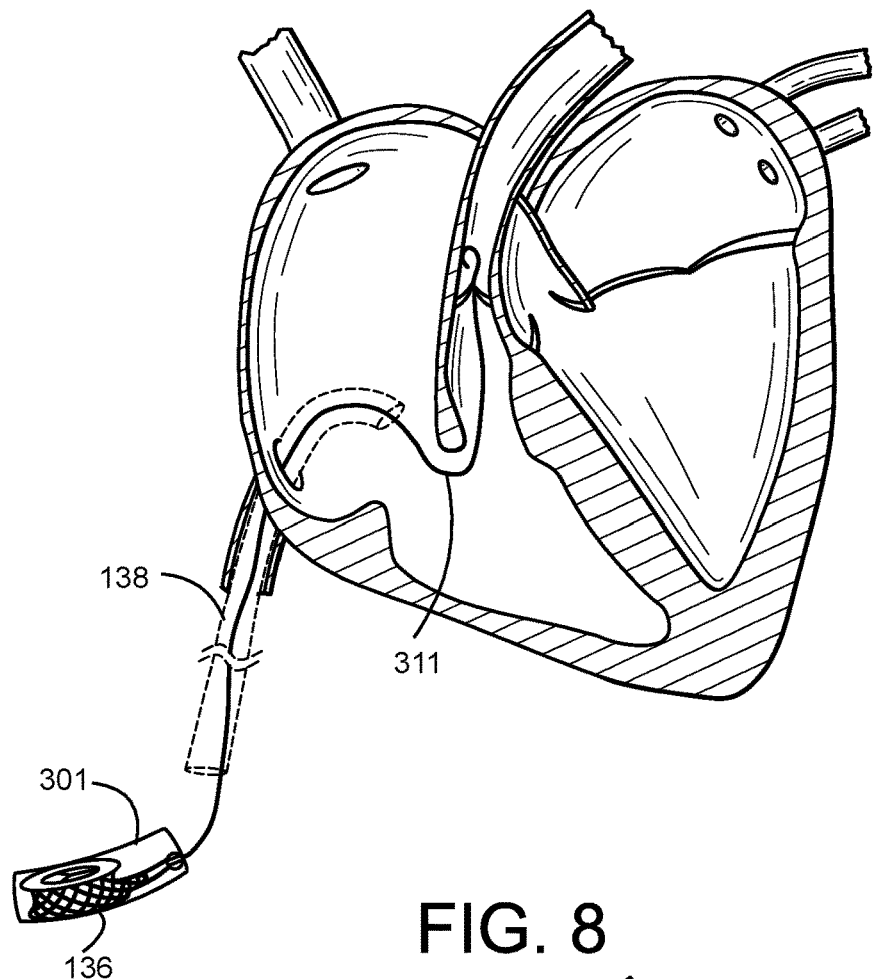

FIG. 7 is an illustration of step 3 of a 6-step process for delivery of an orthogonal prosthetic valve to the tricuspid annulus. FIG. 7 shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

Figure 8:
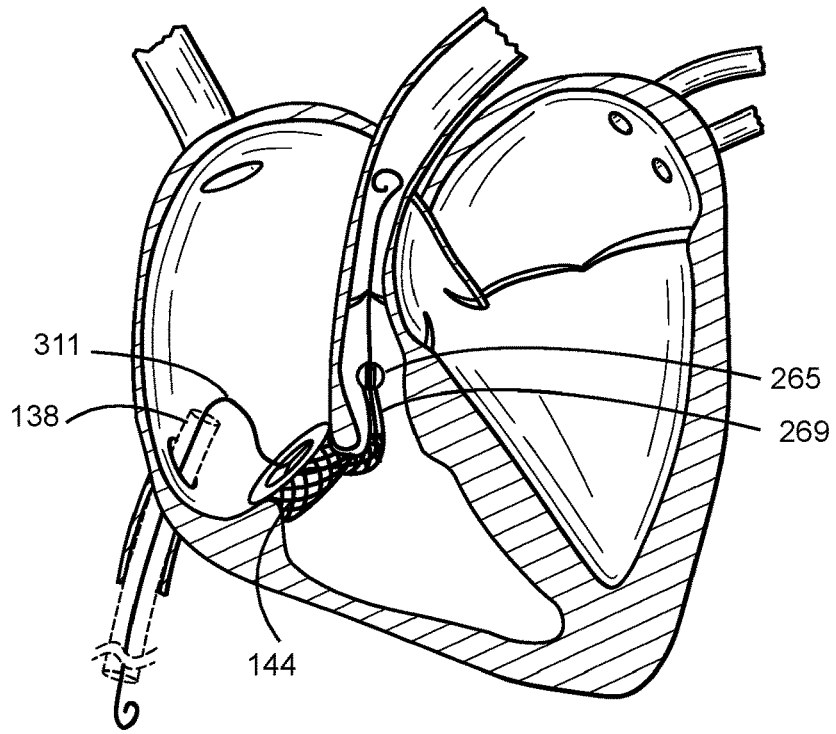

FIG. 8 is an illustration of step 4 of a 6-step process for delivery of an orthogonal prosthetic valve to the tricuspid annulus. FIG. 8 shows the valve advanced up the catheter and deployed into the native annulus by pushing on the outer sheath of the guidewire to pull the valve up the catheter and into position. Tension arm is used to position the valve.

Figure 9:
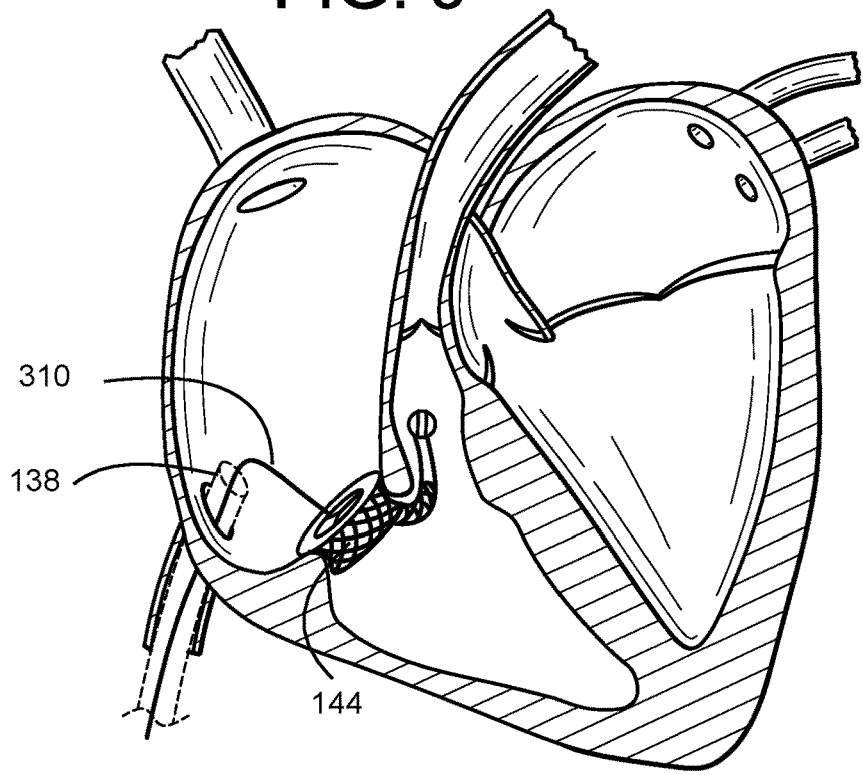

FIG. 9 is an illustration of step 5 of a 6-step process for delivery of an orthogonal prosthetic valve to the tricuspid annulus. FIG. 9 shows a catheter being used to push the proximal side of the valve into position within the annulus.

Figure 10:
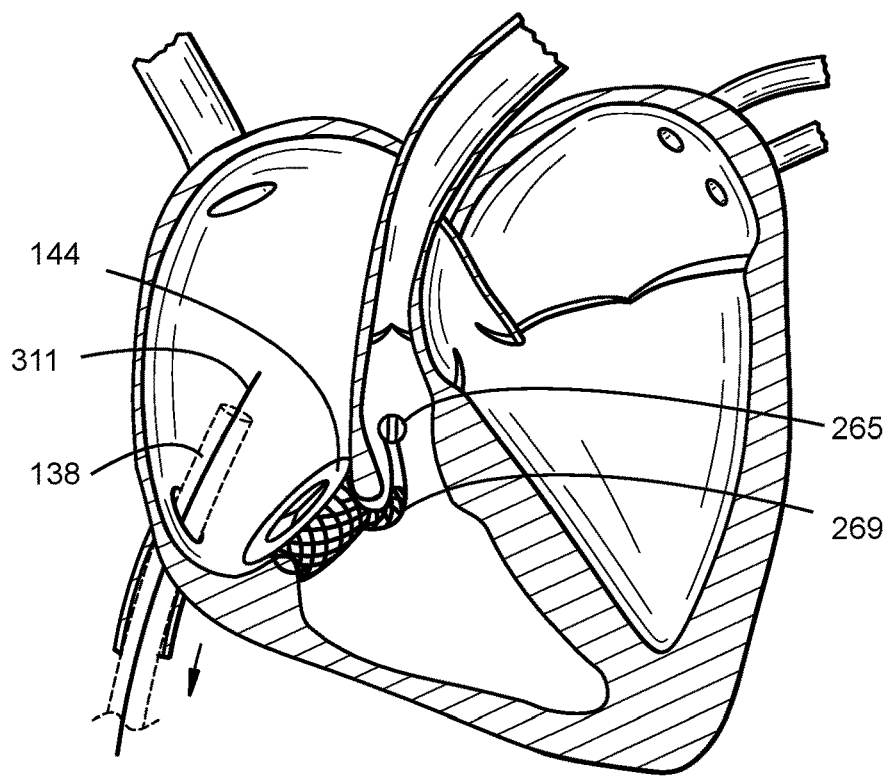

FIG. 10 is an illustration of step 6 of a 6-step process for delivery of an orthogonal prosthetic valve to the tricuspid annulus. FIG. 10 shows withdrawal of the delivery system and anchoring of the proximal side of the valve to the annular tissue.

Figure 11:
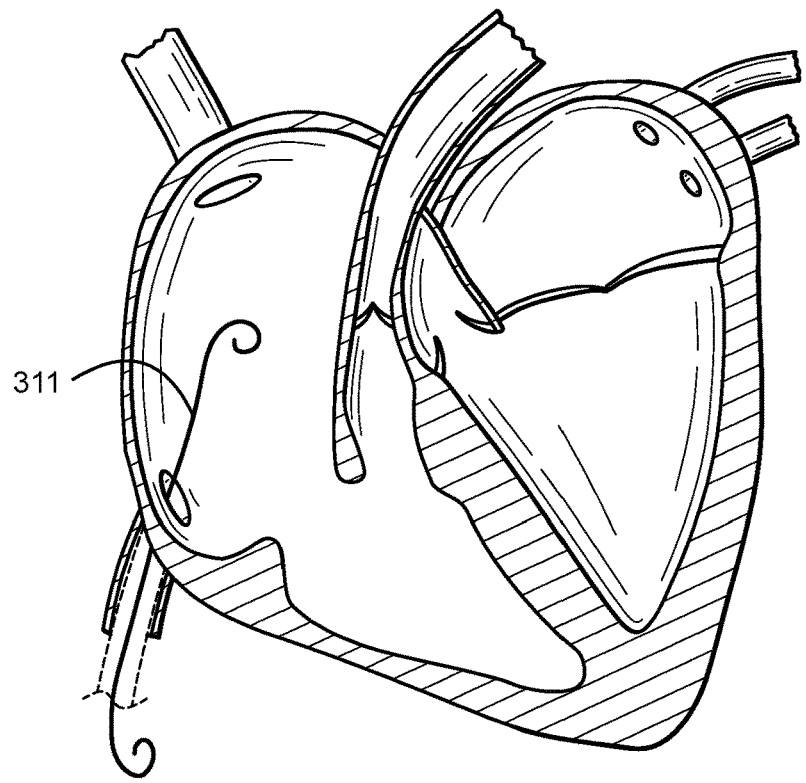

FIG. 11 is an illustration of step 1 of an 8-step process for delivery of an orthogonal prosthetic valve to the tricuspid annulus. FIG. 11 shows an 8 Fr guidewire advanced from the femoral through the inferior vena cava (IVC) to the right atrium.

Figure 12:
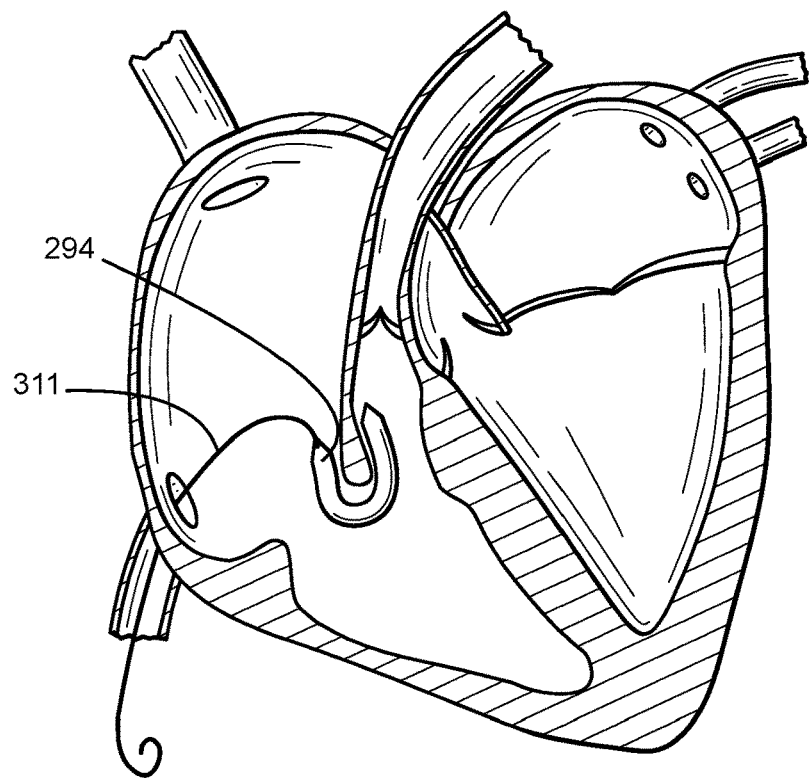

FIG. 12 is an illustration of step 2 of an 8-step process for delivery of an orthogonal prosthetic valve to the tricuspid annulus. FIG. 12 shows a balloon catheter advanced over the guidewire through the native annulus and into the RVOT to expand and push aside valve and leaflet tissue, chordae tendinae that might tangle transcatheter delivery of the valve.

Figure 13:
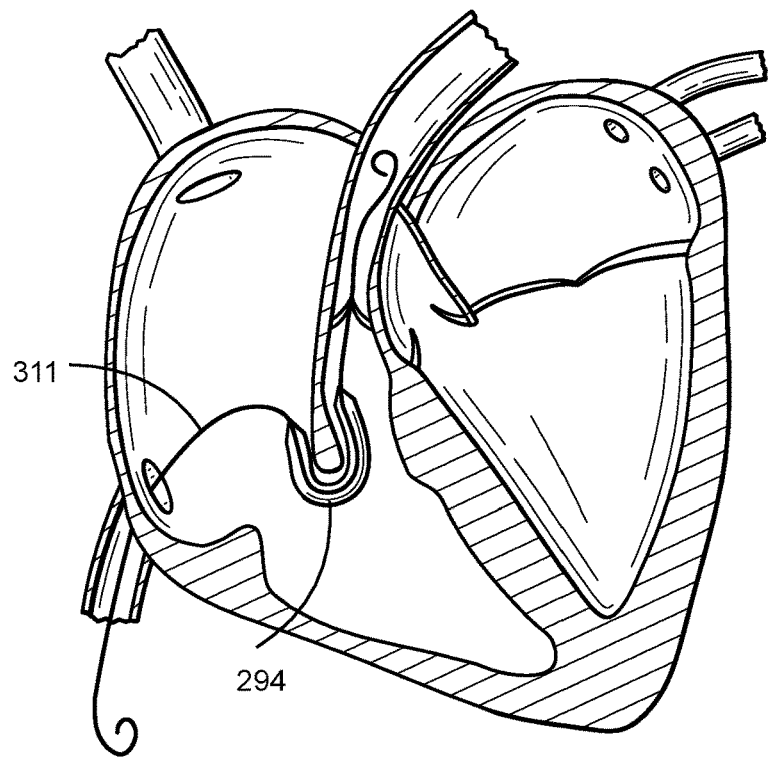

FIG. 13 is an illustration of step 3 of an 8-step process for delivery of an orthogonal prosthetic valve to the tricuspid annulus. FIG. 13 shows an 0.035 guidewire with hypotube sheath delivered to the right ventricular outflow tract (RVOT).

Figure 14:
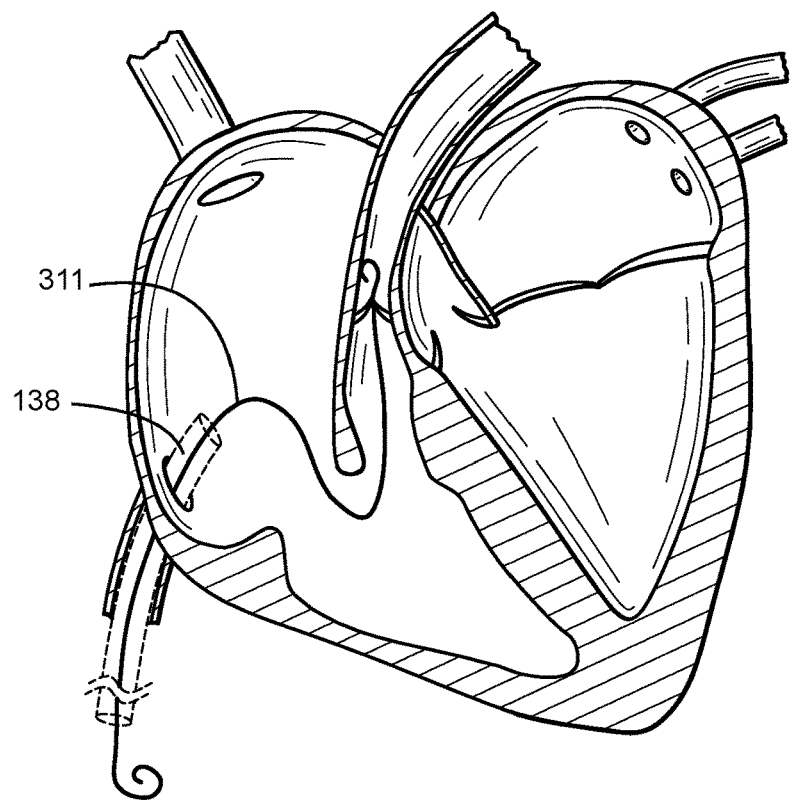

FIG. 14 is an illustration of step 4 of an 8-step process for delivery of an orthogonal prosthetic valve to the tricuspid annulus. FIG. 14 shows a 34 Fr delivery catheter being advanced over the guidewire to and through the native tricuspid annulus to the right ventricle.

Figure 15:
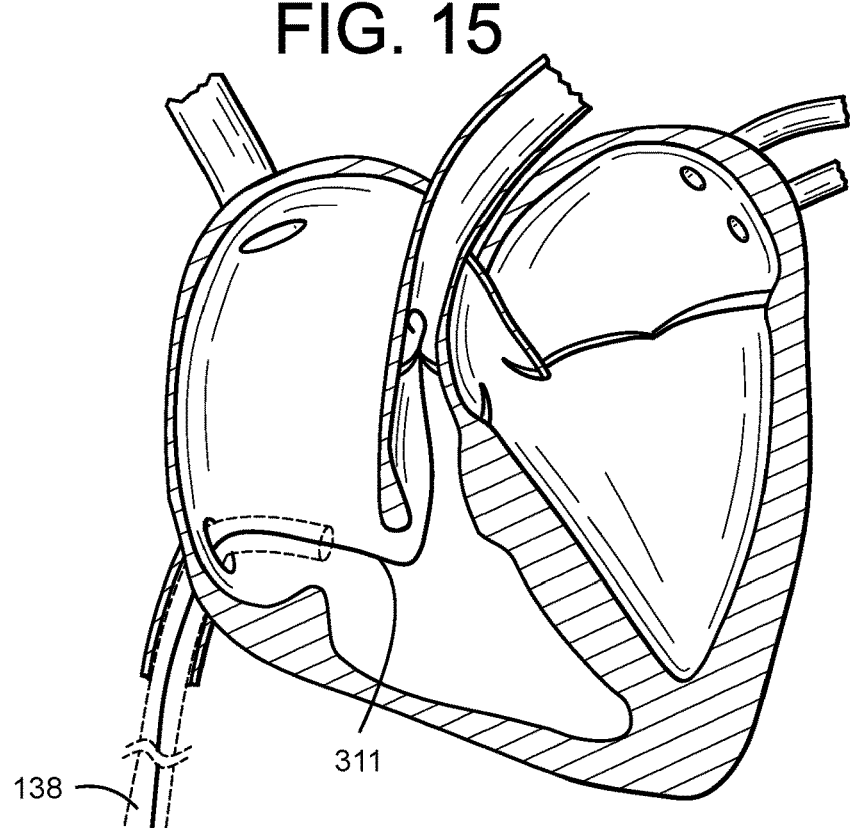

FIG. 15 is an illustration of step 5 of an 8-step process for delivery of an orthogonal prosthetic valve to the tricuspid annulus. FIG. 15 shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

Figure 16:
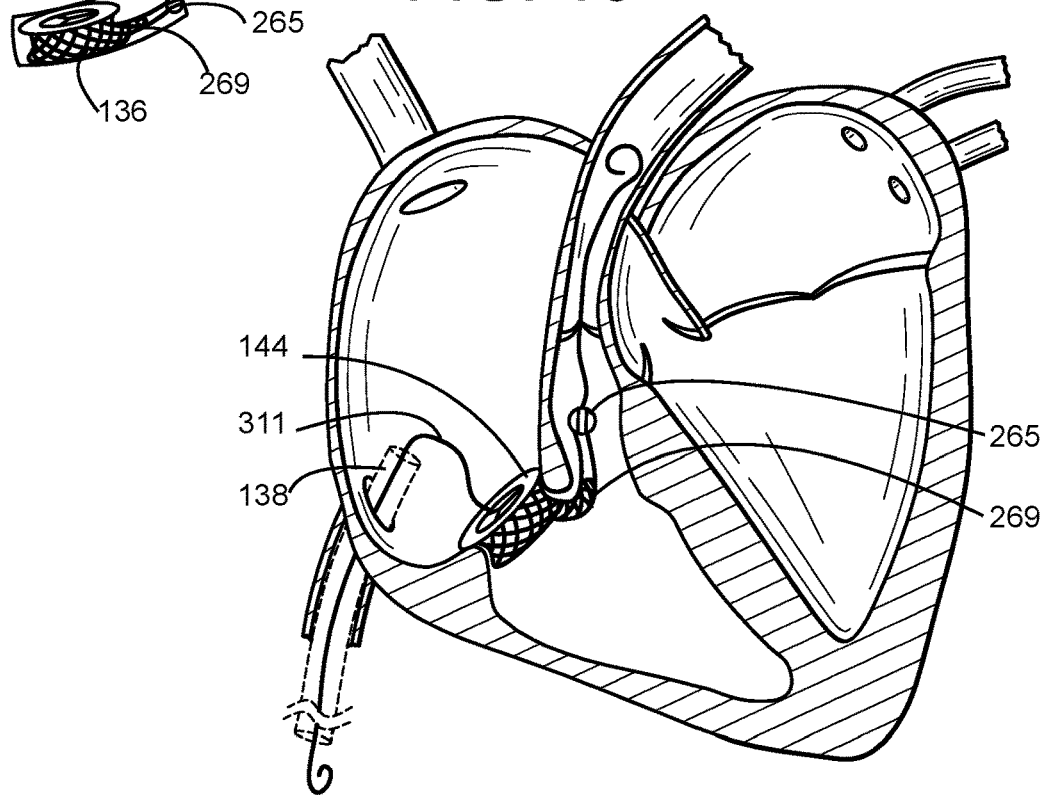

FIG. 16 is an illustration of step 6 of an 8-step process for delivery of an orthogonal prosthetic valve to the tricuspid annulus. FIG. 16 shows the valve advanced up the catheter and deployed into the native annulus by pushing on the outer sheath of the guidewire to pull the valve up the catheter and into position. Tension arm is used to position the valve.

Figure 17:
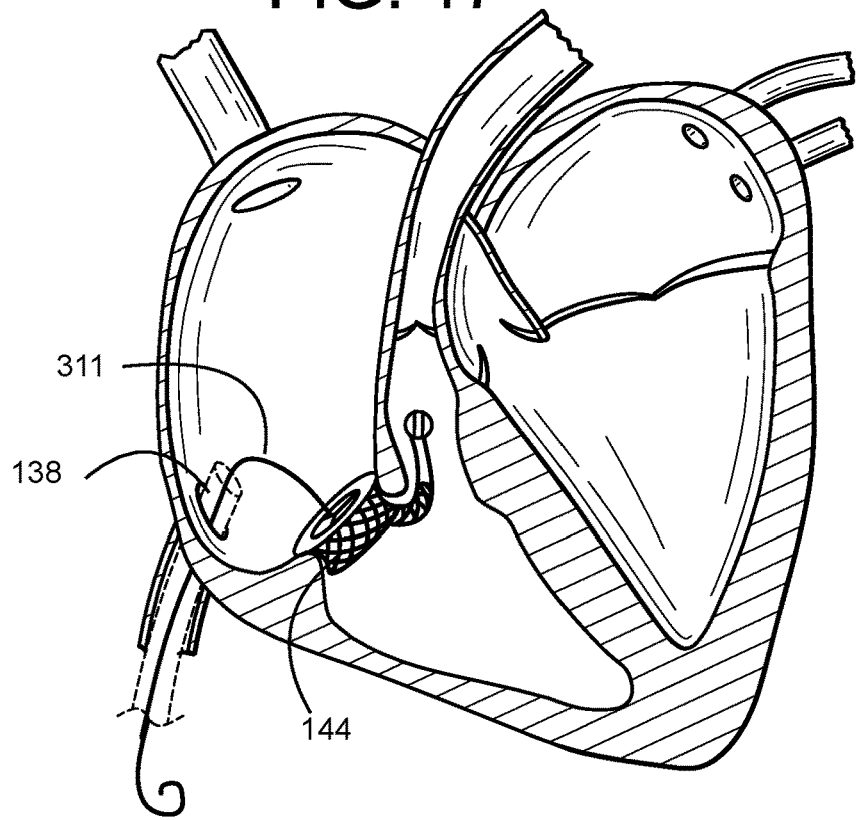

FIG. 17 is an illustration of step 7 of an 8-step process for delivery of an orthogonal prosthetic valve to the tricuspid annulus. FIG. 17 shows a catheter being used to push the proximal side of the valve into position within the annulus.

Figure 18:
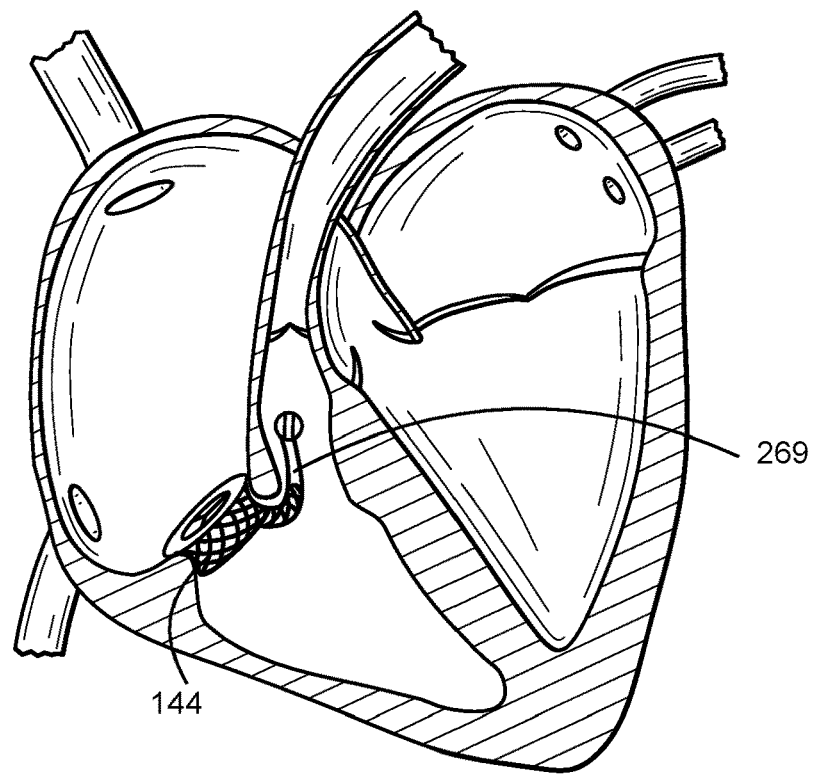

FIG. 18 is an illustration of step 8 of an 8-step process for delivery of an orthogonal prosthetic valve to the tricuspid annulus. FIG. 18 shows withdrawal of the delivery system and anchoring of the proximal side of the valve to the annular tissue.

Figure 19:
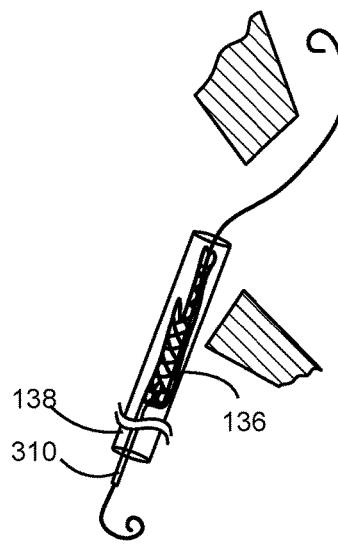

FIG. 19 is an illustration of step 1 of a 6-step process for delivery of an orthogonal prosthetic valve to the tricuspid annulus. FIG. 19 shows the valve advanced up the catheter and deployed into the native annulus.

Figure 20:
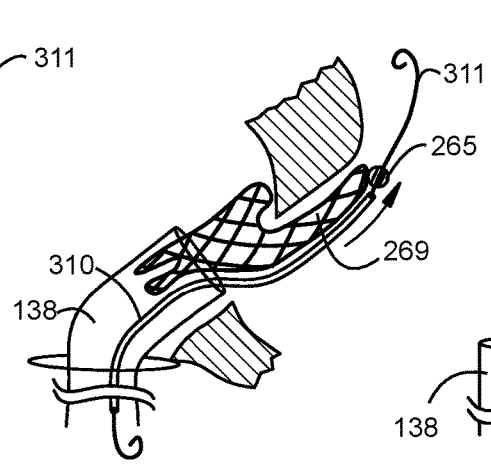

FIG. 20 is an illustration of step 2 of a 6-step process for delivery of an orthogonal prosthetic valve to the tricuspid annulus. FIG. 20 shows pushing on the outer sheath of the guidewire to pull the valve up the catheter and into position, partially expelling the valve with tension arm into the RVOT and the distal side of the valve lodged against the annular wall.

Figure 21:
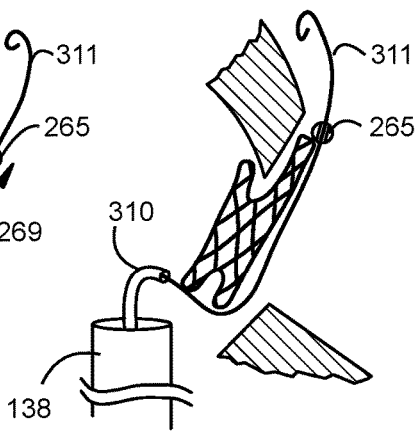

FIG. 21 is an illustration of step 3 of a 6-step process for delivery of an orthogonal prosthetic valve to the tricuspid annulus. FIG. 21 shows a catheter being used to push the proximal side of the valve into position within the annulus.

Figure 22:
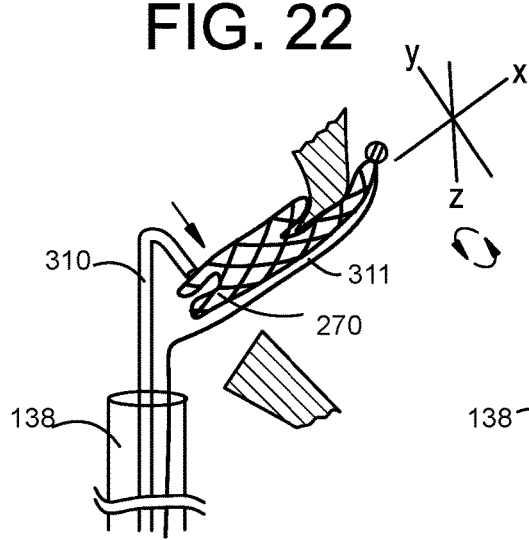

FIG. 22 is an illustration of step 4 of a 6-step process for delivery of an orthogonal prosthetic valve to the tricuspid annulus. FIG. 22 shows how tension arm is used to position the valve while catheter being used to push the proximal side of the valve into position within the annulus.

Figure 23:
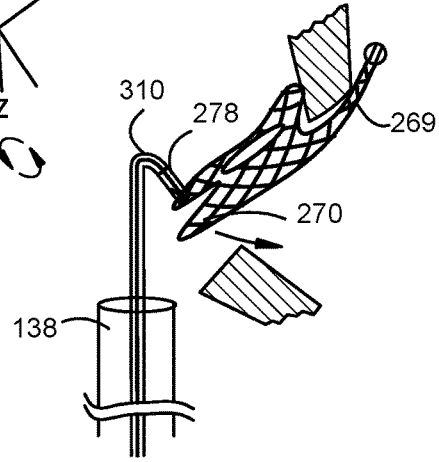

FIG. 23 is an illustration of step 5 of a 6-step process for delivery of an orthogonal prosthetic valve to the tricuspid annulus. FIG. 23 shows how catheter delivers a tissue anchor to secure the proximal side of the valve to the annular tissue.

Figure 24:
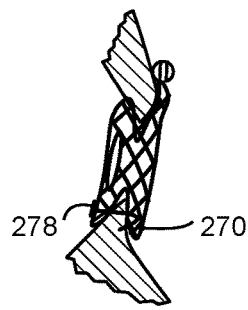

FIG. 24 is an illustration of step 6 of a 6-step process for delivery of an orthogonal prosthetic valve to the tricuspid annulus. FIG. 24 shows withdrawal of the delivery system and anchoring of the proximal side of the valve to the annular tissue.

Figure 25:
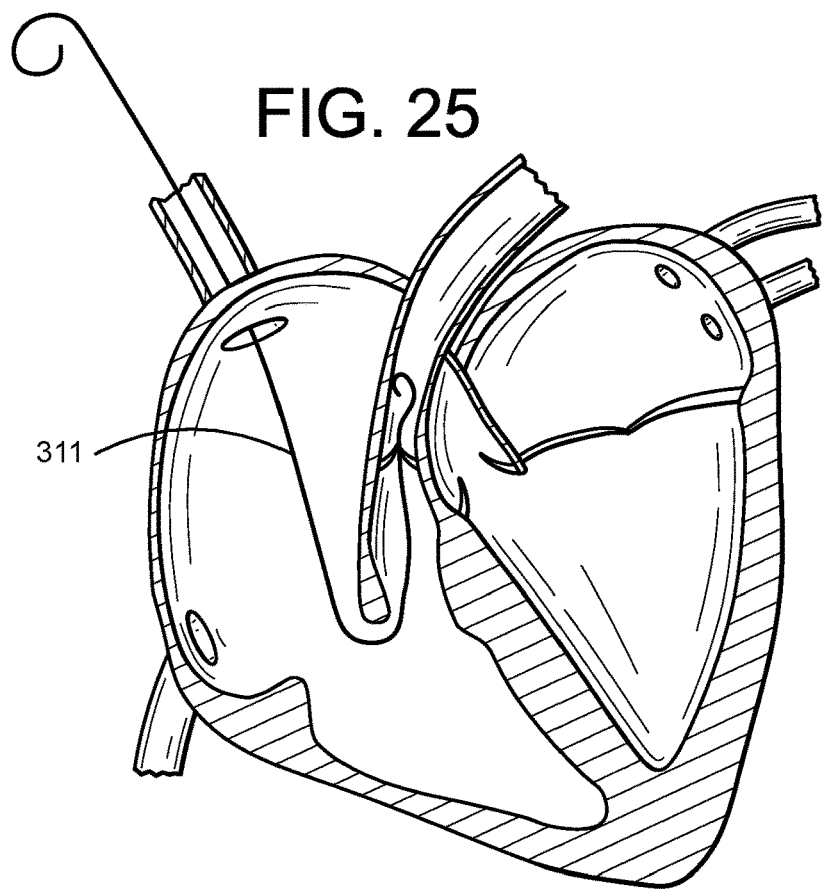

FIG. 25 is an illustration of step 1 of a 6-step process for delivery of a co-axial prosthetic valve to the tricuspid annulus. FIG. 25 shows an 0.035 guidewire with hypotube sheath delivered to the right ventricular outflow tract (RVOT) through the superior vena cava (SVC).

Figure 26:
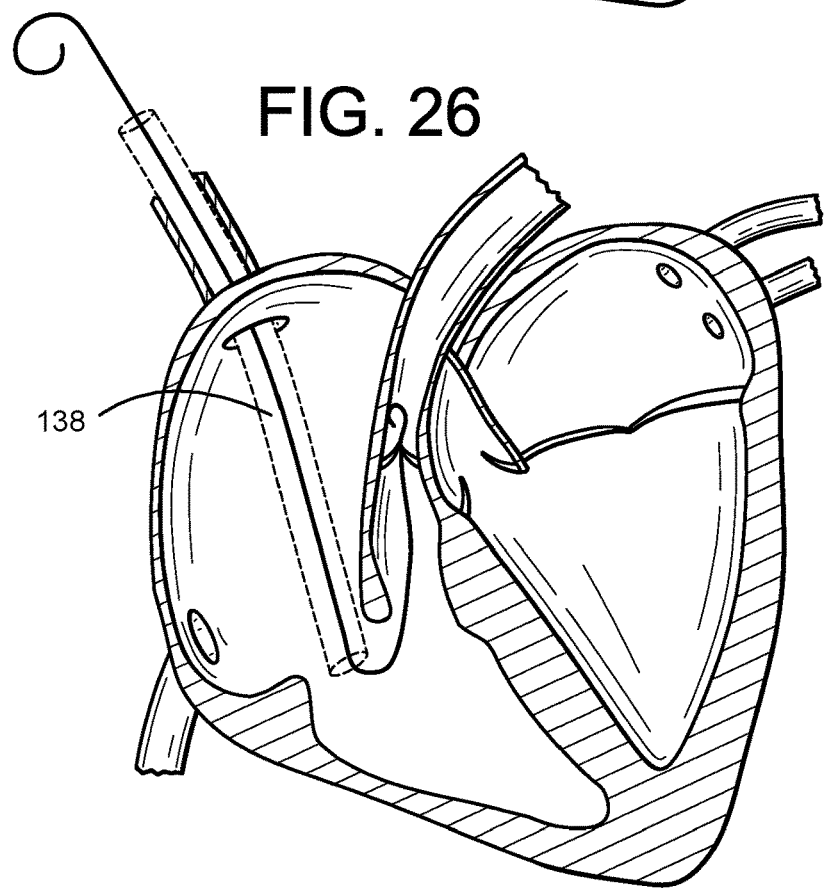

FIG. 26 is an illustration of step 2 of a 6-step process for delivery of a co-axial prosthetic valve to the tricuspid annulus.

FIG. 26 shows a 34 Fr delivery catheter being advanced over the guidewire to and through the native tricuspid annulus to the right ventricle.

Figure 27:
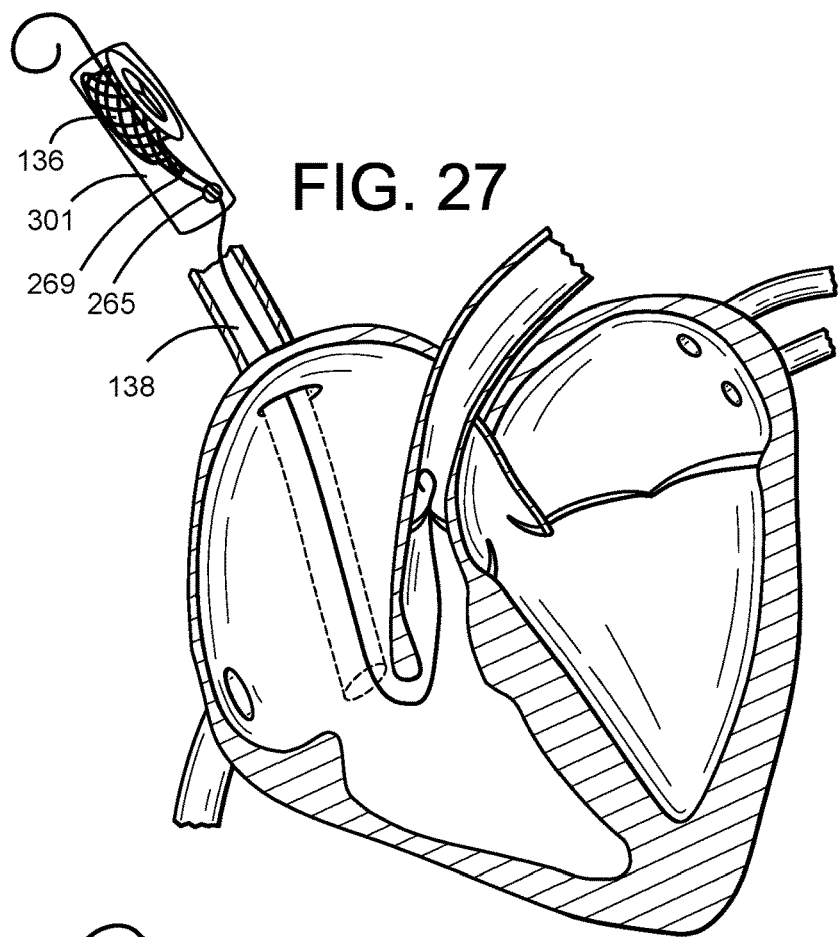

FIG. 27 is an illustration of step 3 of a 6-step process for delivery of a co-axial prosthetic valve to the tricuspid annulus. FIG. 27 shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

Figure 28:
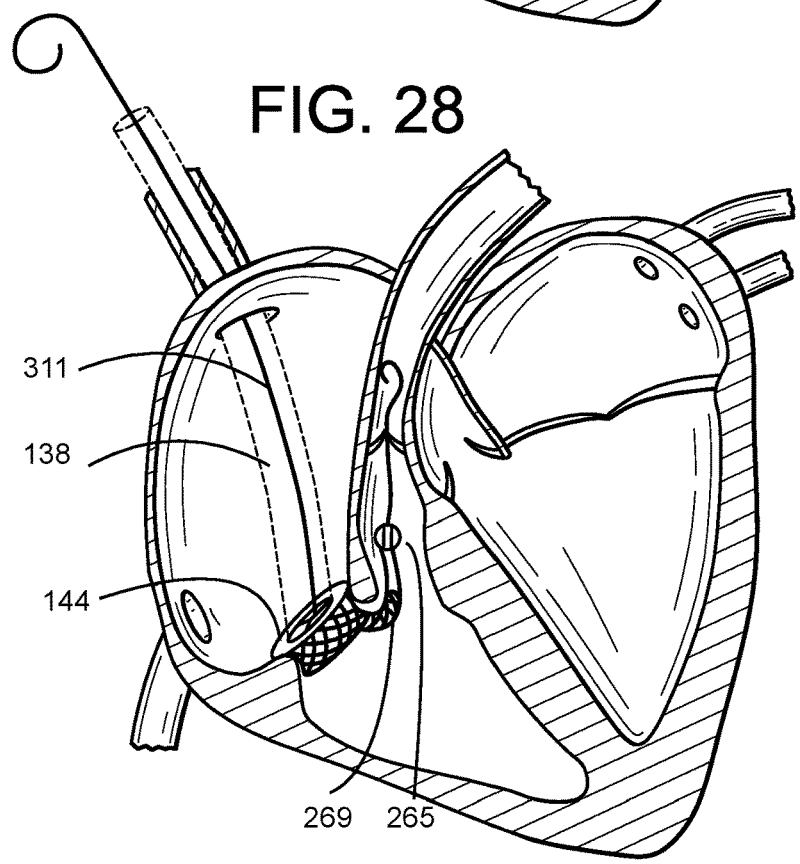

FIG. 28 is an illustration of step 4 of a 6-step process for delivery of a co-axial prosthetic valve to the tricuspid annulus. FIG. 28 shows the valve advanced up the catheter and deployed into the native annulus by pushing on the outer sheath of the guidewire to pull the valve up the catheter and into position. Tension arm is used to position the valve.

Figure 29:
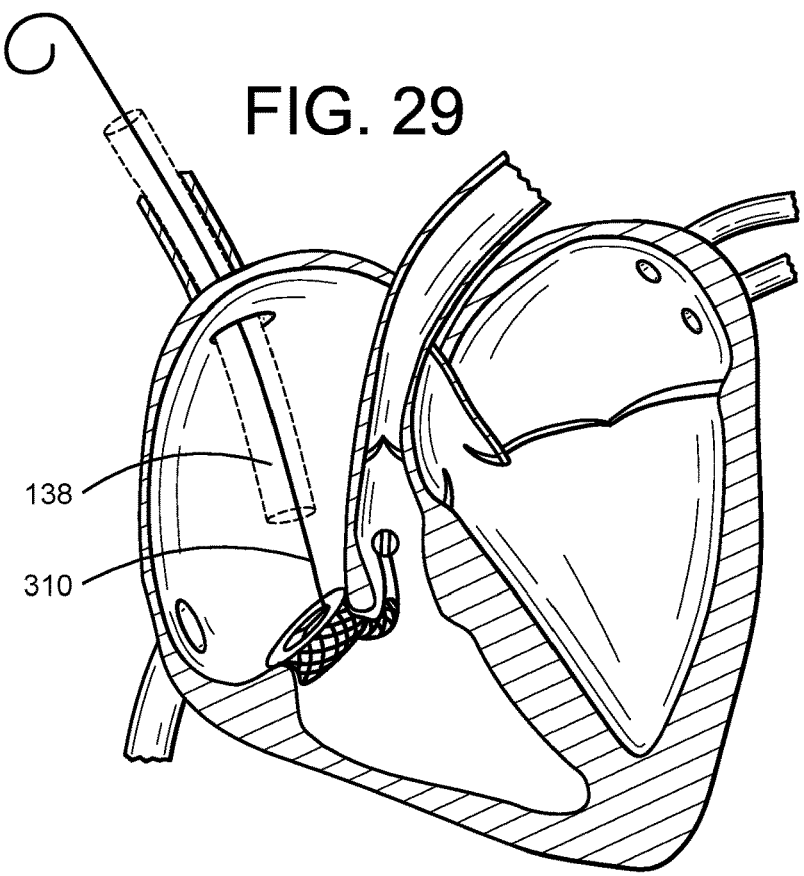

FIG. 29 is an illustration of step 5 of a 6-step process for delivery of a co-axial prosthetic valve to the tricuspid annulus. FIG. 29 shows a catheter being used to push the proximal side of the valve into position within the annulus.

Figure 30:
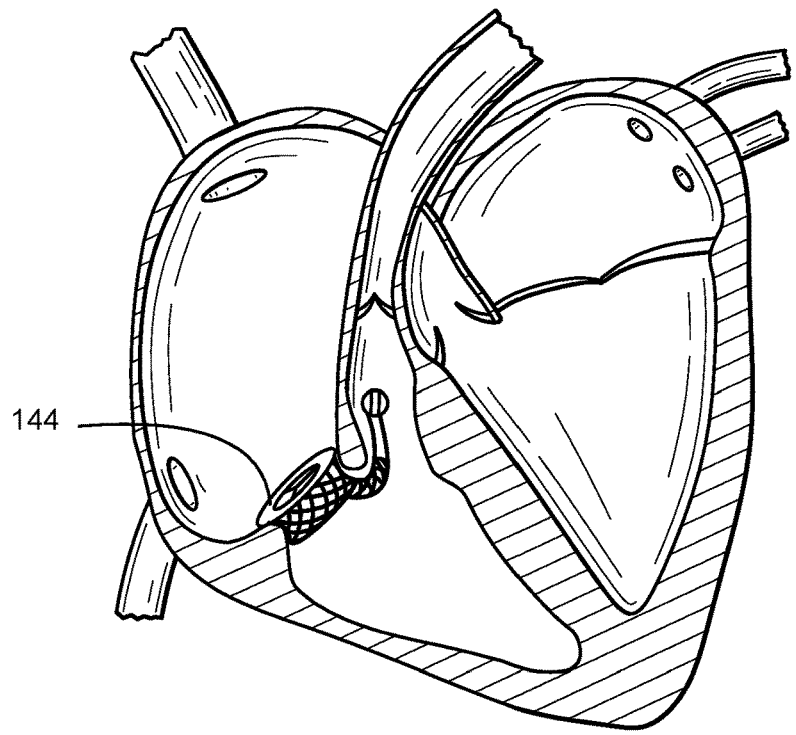

FIG. 30 is an illustration of step 6 of a 6-step process for delivery of a co-axial prosthetic valve to the tricuspid annulus. FIG. 30 shows withdrawal of the delivery system and anchoring of the proximal side of the valve to the annular tissue.

Figure 31:
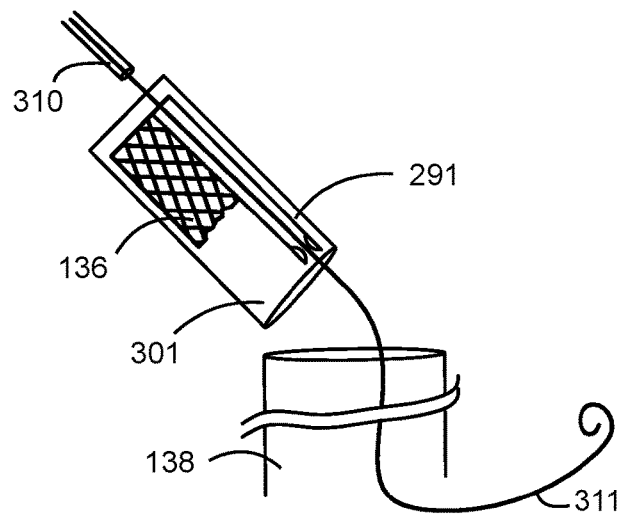

FIG. 31 is an illustration of step 1 of a 4-step process for delivery of a co-axial prosthetic valve to the tricuspid annulus. FIG. 31 shows a co-axial valve being loaded into the distal end of the delivery catheter, with the sheathed guidewire threaded through the tension arm and guidewire collar.

Figure 32:
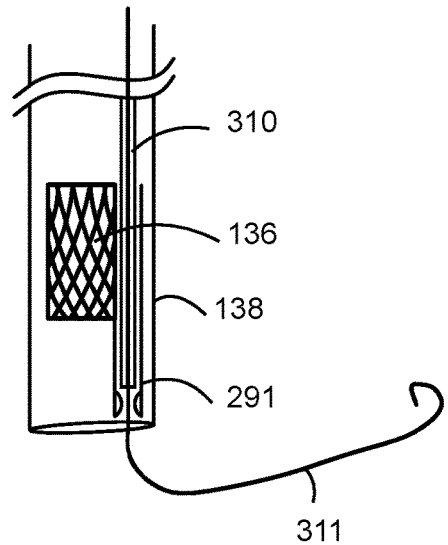

FIG. 32 is an illustration of step 2 of a 4-step process for delivery of a co-axial prosthetic valve to the tricuspid annulus. FIG. 32 shows a co-axial valve being delivered to the proximal end of the delivery catheter, with the sheathed guidewire threaded through the tension arm and guidewire collar.

Figure 33:
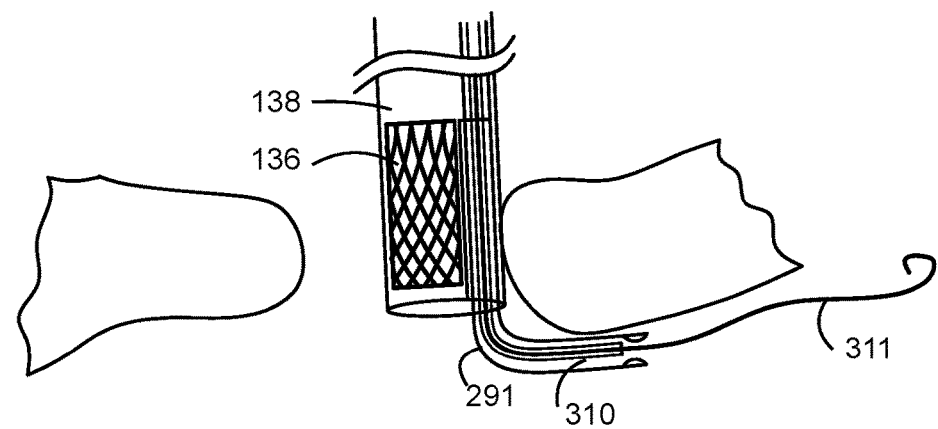

FIG. 33 is an illustration of step 3 of a 4-step process for delivery of a co-axial prosthetic valve to the tricuspid annulus. FIG. 33 shows a co-axial valve partially expelled from the delivery catheter, with the tension arm and guidewire collar being positioned into the RVOT.

Figure 34:
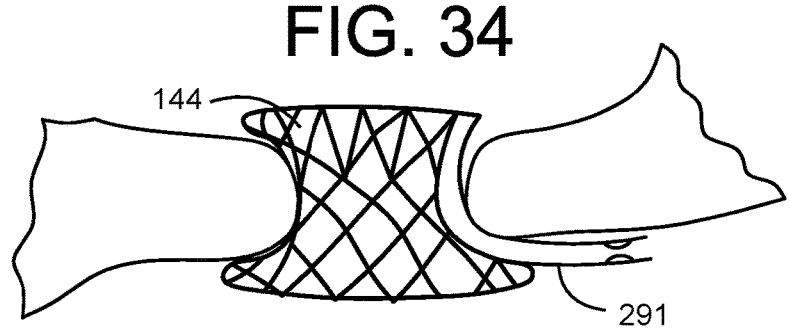

FIG. 34 is an illustration of step 4 of a 4-step process for delivery of a co-axial prosthetic valve to the tricuspid annulus. FIG. 34 shows that, once positioned, the self-expanding the valve can be completely expelled from the delivery catheter and deployed as a prosthetic valve.

Figure 35:
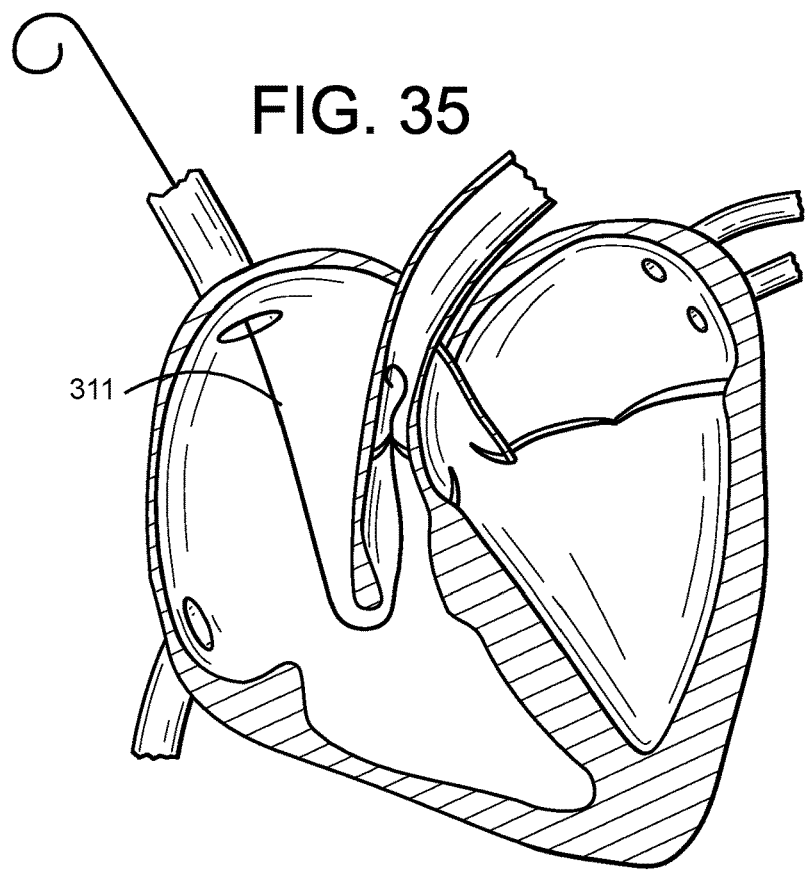

FIG. 35 is an illustration of step 1 of a 7-step process for delivery of a co-axial prosthetic valve to the tricuspid annulus. FIG. 35 shows an 0.035 guidewire with hypotube sheath delivered to the right ventricular outflow tract (RVOT) through the superior vena cava (SVC).

Figure 36:
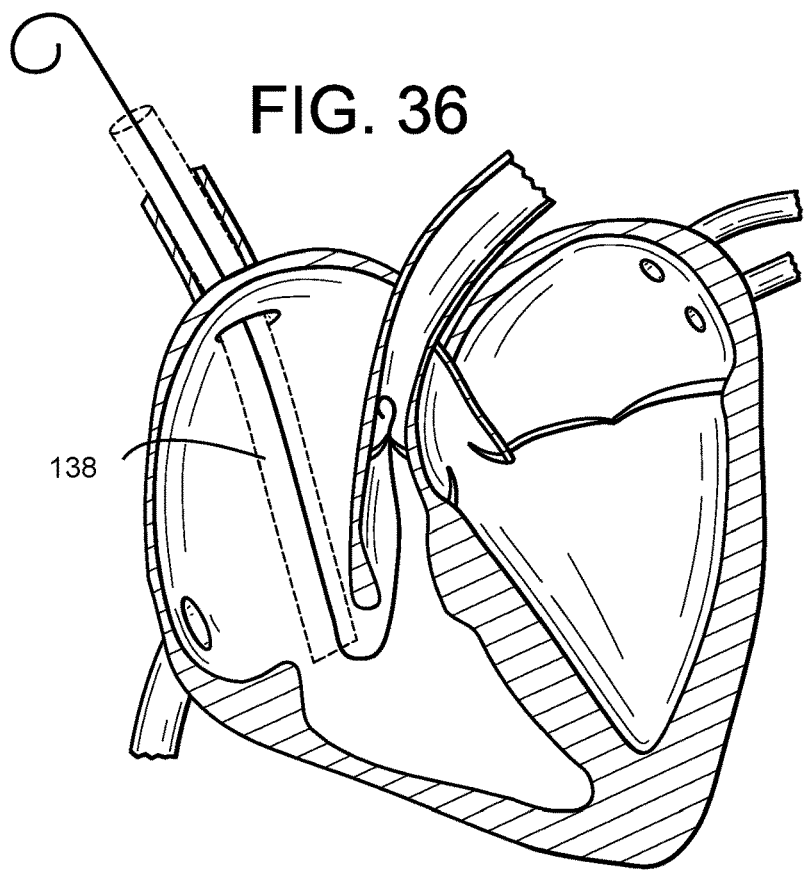

FIG. 36 is an illustration of step 2 of a 7-step process for delivery of a co-axial prosthetic valve to the tricuspid annulus. FIG. 36 shows a 34 Fr delivery catheter being advanced over the guidewire to and through the native tricuspid annulus to the right ventricle.

Figure 37:
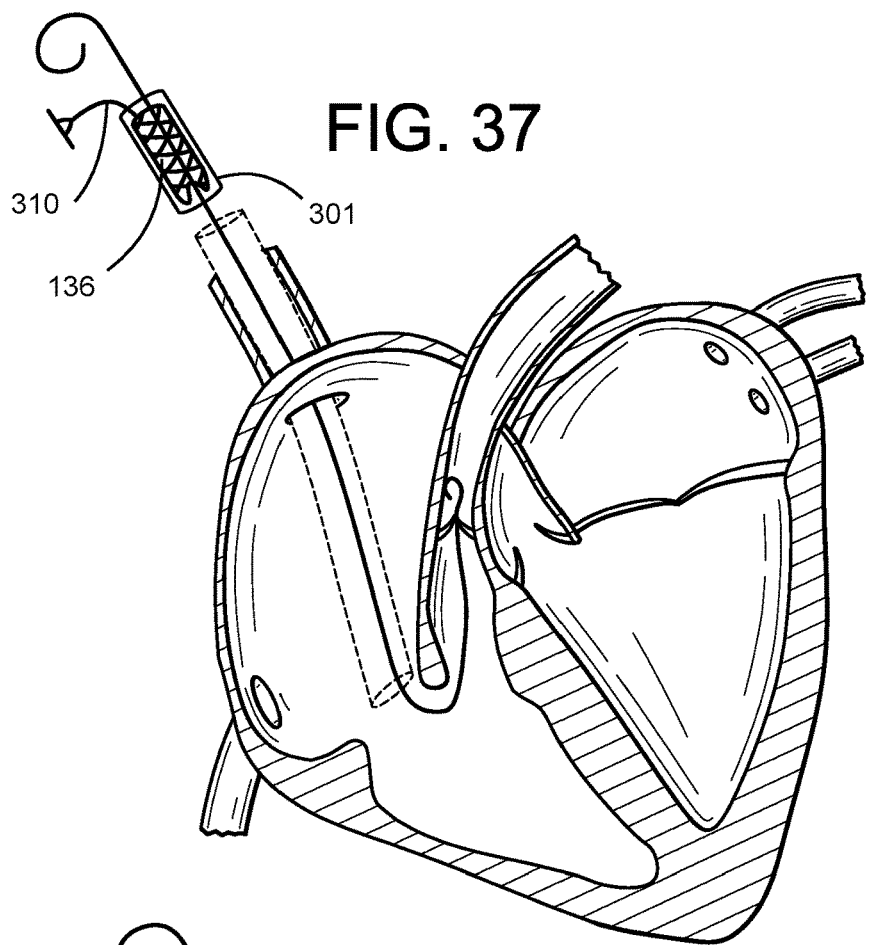

FIG. 37 is an illustration of step 3 of a 7-step process for delivery of a co-axial prosthetic valve to the tricuspid annulus. FIG. 37 shows a capsule having a compressed valve therein where the capsule is loaded into the proximal end of the delivery catheter and the valve is withdrawn from the capsule into the delivery catheter, with sheathed guidewire threaded through the valve and providing a wire path to the RVOT, planned deployment location.

Figure 38:
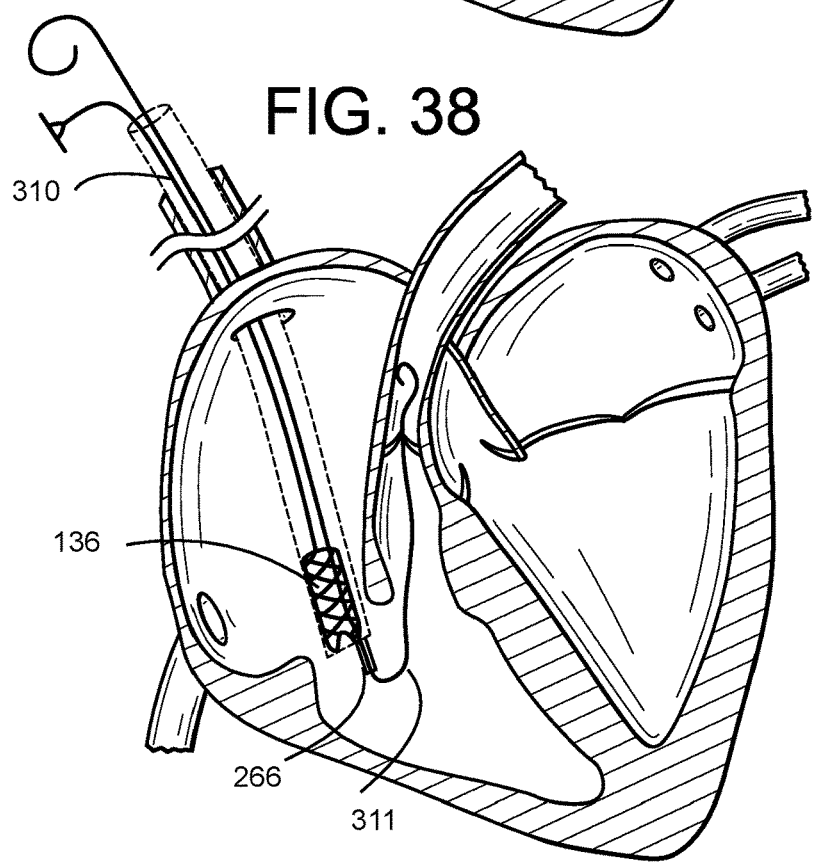

FIG. 38 is an illustration of step 4 of a 7-step process for delivery of a co-axial prosthetic valve to the tricuspid annulus. FIG. 38 shows the valve advanced up the catheter and deployed into the native annulus by pushing on the outer sheath of the guidewire to pull the valve up the catheter and into position. Tension arm is used to position the valve.

Figure 39:
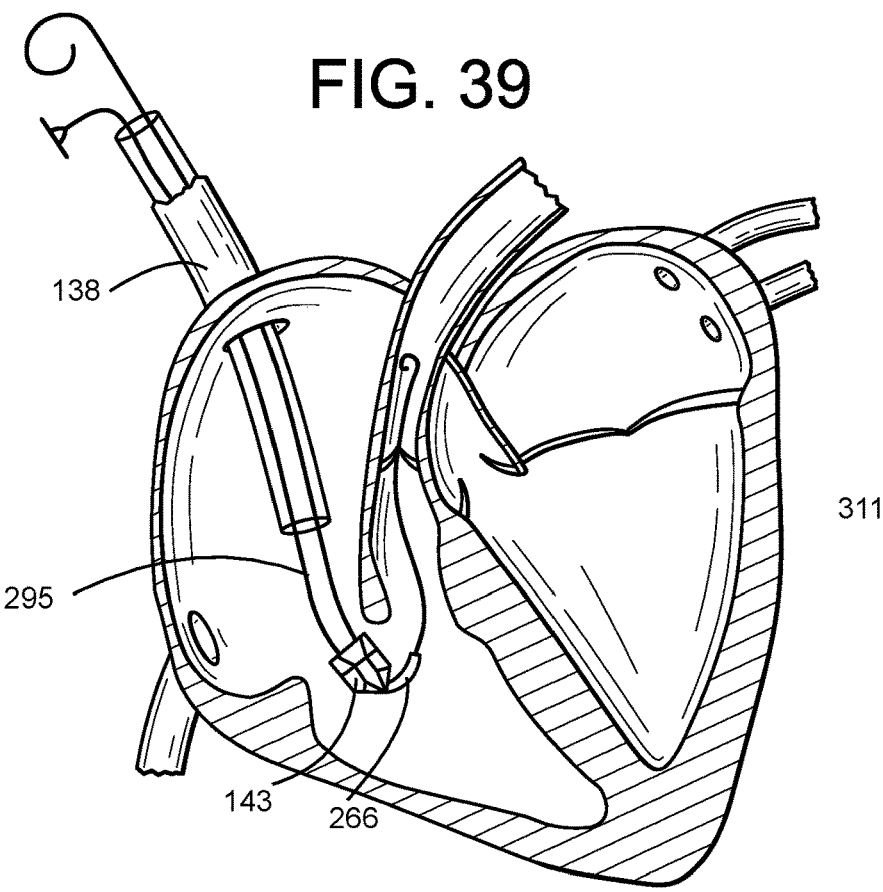

FIG. 39 is an illustration of step 5 of a 7-step process for delivery of a co-axial prosthetic valve to the tricuspid annulus. FIG. 39 shows a catheter being used to push the proximal side of the valve into position within the annulus.

Figure 40:
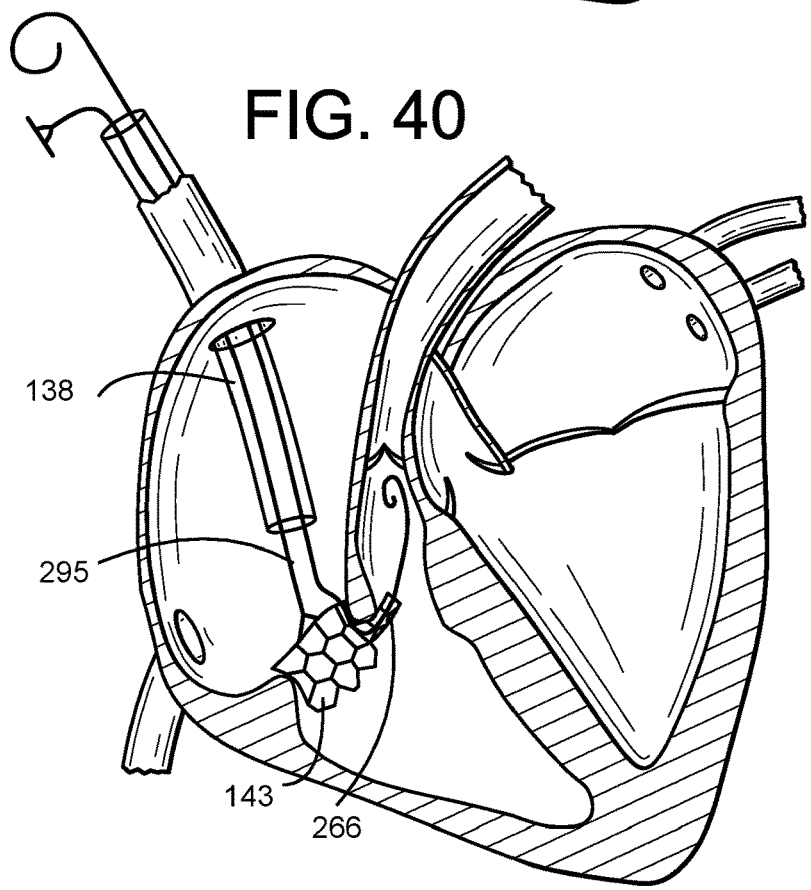

FIG. 40 is an illustration of step 6 of a 7-step process for delivery of a co-axial prosthetic valve to the tricuspid annulus. FIG. 40 shows balloon expansion of the co-axial valve in the native annulus and anchoring of the proximal side of the valve to the annular tissue.

Figure 41:
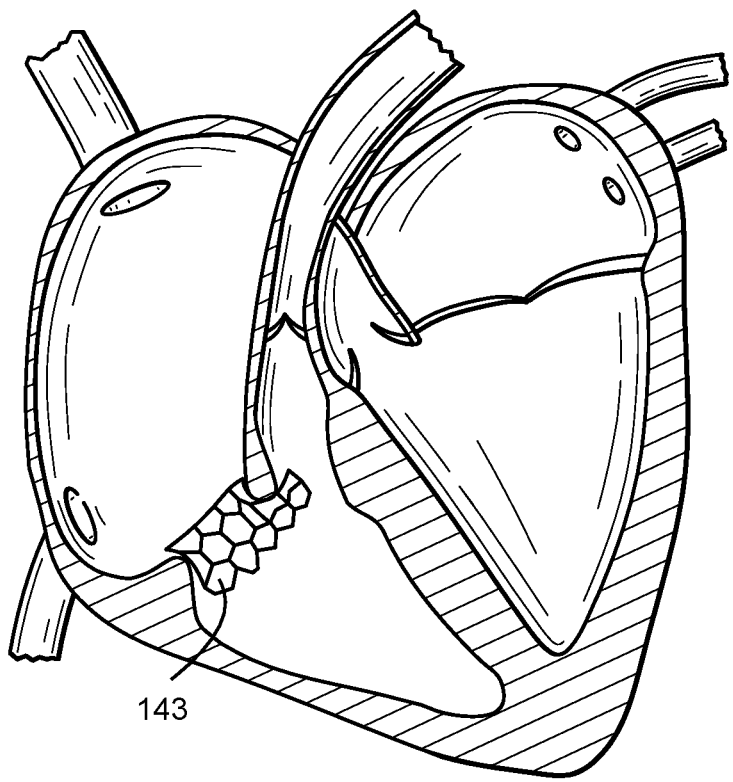

FIG. 41 is an illustration of step 7 of a 7-step process for delivery of a co-axial prosthetic valve to the tricuspid annulus. FIG. 41 shows withdrawal of the delivery system and anchoring of the proximal side of the valve to the annular tissue.

Figure 42:
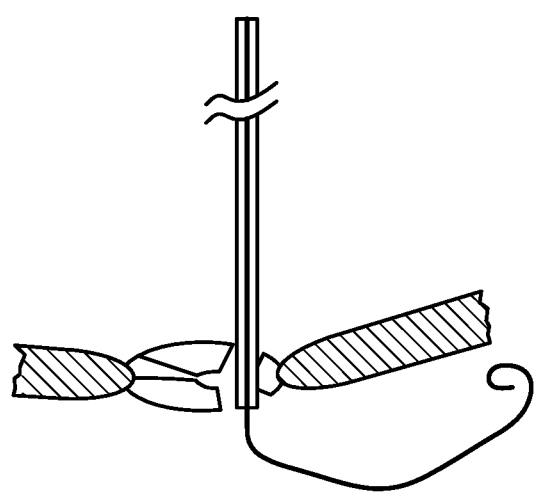

FIG. 42 is an illustration of step 1 of a 6-step process for delivery of a co-axial prosthetic valve to the tricuspid annulus. FIG. 42 shows the delivery catheter deployed to the native annulus.

Figure 43:
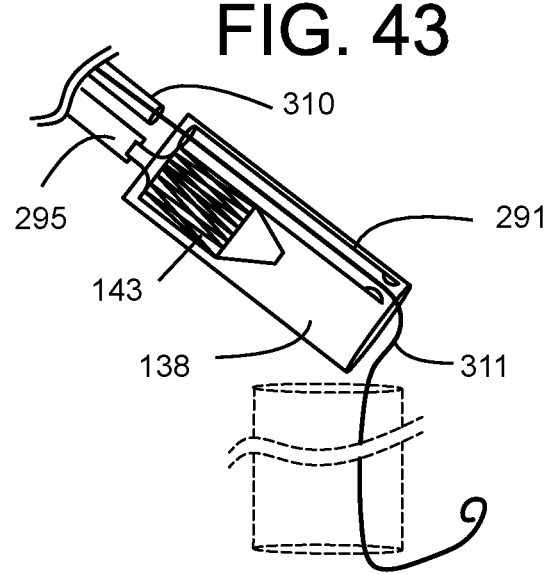

FIG. 43 is an illustration of step 2 of a 6-step process for delivery of a co-axial prosthetic valve to the tricuspid annulus. FIG. 43 shows a co-axial valve being loaded into the delivery catheter, with the sheathed guidewire threaded through the tension arm and guidewire collar.

FIG. 44 is an illustration of step 3 of a 6-step process for delivery of a co-axial prosthetic valve to the tricuspid annulus. FIG. 44 shows a co-axial valve being delivered to the proximal end of the delivery catheter, with the sheathed guidewire threaded through the tension arm and guidewire collar.

FIG. 45 is an illustration of step 4 of a 6-step process for delivery of a co-axial prosthetic valve to the tricuspid annulus. FIG. 45 shows a co-axial valve partially expelled from the delivery catheter, with the tension arm and guidewire collar being positioned into the RVOT.

FIG. 46 is an illustration of step 5 of a 6-step process for delivery of a co-axial prosthetic valve to the tricuspid annulus. FIG. 46 shows that, once positioned, the balloon-expanding co-axial valve can be completely deployed into the inner circumference of the native annulus to function as a prosthetic valve.

FIG. 47 is an illustration of step 6 of a 6-step process for delivery of a co-axial prosthetic valve to the tricuspid annulus. FIG. 47 shows the deployed valve.

DETAILED DESCRIPTION OF THE PREFERRED EMBODIMENTS

The invention is directed to a transcatheter heart valve replacement that is a low profile, orthogonally delivered implantable prosthetic valve having an ring-shaped tubular frame, an inner 2- or 3-panel sleeve, an elongated sub-annular tension arm extending into the right ventricular outflow tract, and one or more anchor elements.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Side-Delivery or Orthogonal Delivery

In the description and claims herein, the terms "side-delivered", "side-delivery", "orthogonal", "orthogonally delivered" and so forth are used to describe that the valves of the present invention are compressed and delivered at a roughly 90 degree angle compared to traditional transcatheter heart valves. Orthogonal delivery is a transverse delivery where a perimeter distal sidewall exits the delivery catheter first, followed by the central aperture, followed by the proximal sidewall.

Traditional valves have a central cylinder axis that is parallel to the length-wise axis of the delivery catheter and are deployed from the end of the delivery catheter and expanded radially outward from the central annular axis, in a manner akin to pushing a closed spring-loaded umbrella out of a sleeve to make it spring open. However, the valves of the present invention are compressed and delivered in a sideways manner. To begin with the shape of the expanded valve is that of a large diameter shortened cylinder with an extended collar or cuff. The valves are compressed, in one preferred embodiment, where the central axis of the valve is roughly perpendicular to (orthogonal to) the length-wise axis of the delivery catheter. In one preferred embodiment, the valves are compressed vertically, similar to collapsing the height of a cylinder accordion-style from taller to shorter, and the valves are also compressed by folding a front panel against a back panel. In another preferred embodiment, the valves may be compressed by rolling.

Traditional valves can only be expanded as large as what the internal diameter of the delivery catheter will allow. Efforts to increase the expanded diameter of traditional valves have run into the problems of trying to compress too much material and structure into too little space.

Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, eg. from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In one preferred embodiment of the invention, the transcatheter approach includes advancing to the tricuspid valve/right atrium of the heart through the inferior vena cava via the femoral vein, (ii) advancing to the tricuspid valve/right atrium of the heart through the superior vena cava via the jugular vein, (iii) advancing to the tricuspid valve/right atrium of the heart through a trans-atrial approach, e.g. fossa ovalis or lower.

In another preferred embodiment of the invention, the transcatheter approach includes (i) advancing to the mitral valve or pulmonary artery of the heart through the inferior vena cava via the femoral vein, (ii) advancing to the mitral valve or pulmonary artery of the heart through the superior vena cava via the jugular vein, (iii) advancing to the mitral valve of the heart through a trans-atrial approach, e.g. fossa ovalis or lower, via the IVC-femoral or the SVC-jugular approach.

Annular Support Frame

In the description and claims herein, the term "annular support frame", and also "wire frame" or "flange or "collar" refers to a three-dimensional structural component that is seated within a native valve annulus and is used as a mounting element for a leaflet structure, a flow control component, or a flexible reciprocating valve.

In a preferred embodiment, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the back wall portion can be further defined as having a back upper collar portion and a back lower body portion.

The annular (outer) support frame has a flow control component mounted within the annular support frame and configured to permit blood flow in a first direction through an inflow end of the valve and block blood flow in a second direction, opposite the first direction, through an outflow end of the valve.

Since the outer frame is preferably made of superelastic metal or alloy such as Nitinol, the frame is compressible. Preferably, the outer frame is constructed of a plurality of compressible wire cells having a orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as Nitinol or similar alloy, wherein the annular support frame is formed by manufacturing the structural material as a braided wire frame, a laser-cut wire frame, or a wire loop. The annular support frame is about 5-60 mm in height, has an outer diameter dimension, R, of 30-80 mm, and an inner diameter dimension of 31-79 mm, accounting for the thickness of the wire material itself. As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. In one preferred embodiment, the annular support frame used in the prosthetic heart valve deployed in the mitral annulus may have a complex shape determined by the anatomical structures where the valve is being mounted. For example, in the mitral annulus, the circumference of the mitral valve may be a rounded ellipse, the septal wall is known to be substantially vertical, and the mitral is known to enlarge in disease states. Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron®.

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Valve Frame Optional Atrial Sealing Collars

The valve frame may optionally have a separate atrial sealing collar attached to the upper (atrial) edge of the frame, for deploying on the atrial floor, that is used to direct blood from the atrium into the sleeve and to seal against blood leakage around the valve frame. The valve frame may also optionally have a separate ventricular sealing collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial sealing collar, and optionally to attach to and support the sleeve/conduit.

Annular Support Frame Delivery

The valve frame/annular support frame may be compressed for transcatheter delivery and may be expandable as a self-expandable shape-memory element or using a transcatheter expansion balloon. Some embodiments may have both an atrial sealing collar and a ventricular sealing collar, whereas other embodiments within the scope of the invention include prosthetic valves having either a single atrial sealing collar, a single ventricular sealing collar, or having no additional sealing collar structure.

Frame Material

Preferably, the frame is made from a superelastic metal component, such as laser-cut Nitinol tube, or flat sheet or other similarly functioning material such as braided wire. The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from Nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required mechanical behavior.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard Nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a Nitinol wire and a simple braiding fixture. The wire is wound on the braiding fixture in a pattern until an isodiametric tube is formed. Secondarily, the braided wire frame is placed on a shaping fixture and processed using industry standard Nitinol shape forming methods.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to a tubular frame, to function as a prosthetic valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to the native annular tissue, usually at or near the periphery of the atrial sealing collar. The anchor may be positioned to avoid piercing tissue and just rely on the compressive force of the two plate-like sealing collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the sealing collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of, the flexible sleeve. The sleeve may be unattached to the support post, or the sleeve may be directly or indirectly attached to the support post.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

Displacement—The volume of fluid displaced by one complete stroke or revolution

Ejection fraction is a measurement of the percentage of blood leaving your heart each time it contracts. During each heartbeat pumping cycle, the heart contracts and relaxes. When your heart contracts, it ejects blood from the two pumping chambers (ventricles)

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Force—A push or pull acting upon a body. In a hydraulic cylinder, it is the product of the pressure on the fluid, multiplied by the effective area of the cylinder piston.

Prosthetic Valve

The term "valve prosthesis" or "prosthetic valve" refers to a combination of a frame and a leaflet or flow control structure, and encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Tethers

The tethers are made from surgical-grade materials such as biocompatible polymer suture material. Non-limiting examples of such material include ultra high-molecular weight polyethylene (UHMWPE), 2-0 exPFTE(polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines-Anchors-Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether-capture mechanisms built into the tethering face of the anchor(s). Anchors may also have in-growth material, such as polyester fibers, to promote in-growth of the anchors into the myocardium.

In one embodiment, a prosthetic valve frame may include an atrial sealing collar, a ventricular sealing collar, or both.

Tube and/or Cover Material—Biological Tissue

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance-Cyprus Limited disclosing a covered stent assembly, U.S. Pat. No. 6,440,164 to Scimed Life Systems, Inc. disclosing a bioprosthetic valve for implantation, and U.S. Pat. No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316 L stainless steel wire frame as base for the drug Tacrolimus and utilizing integrated turbostratic carbofilm as the drug carrier. VESTA sync (MIV Therapeutics) using GenX stainless steel (316 L) as base utilizing microporous hydroxyapatite coating as carrier for the drug Sirolimus. YUKON choice (Translumina) used 316 L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316 L stainless steel coated with polyethylene vinyl acetate (PEVA) and poly-butyl methacrylate (PBMA) for carrying the drug Sirolimus. Taxus (Boston Scientific) utilizes 316 L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316 L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316 L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

DRAWING FIGURES

Figure 1:
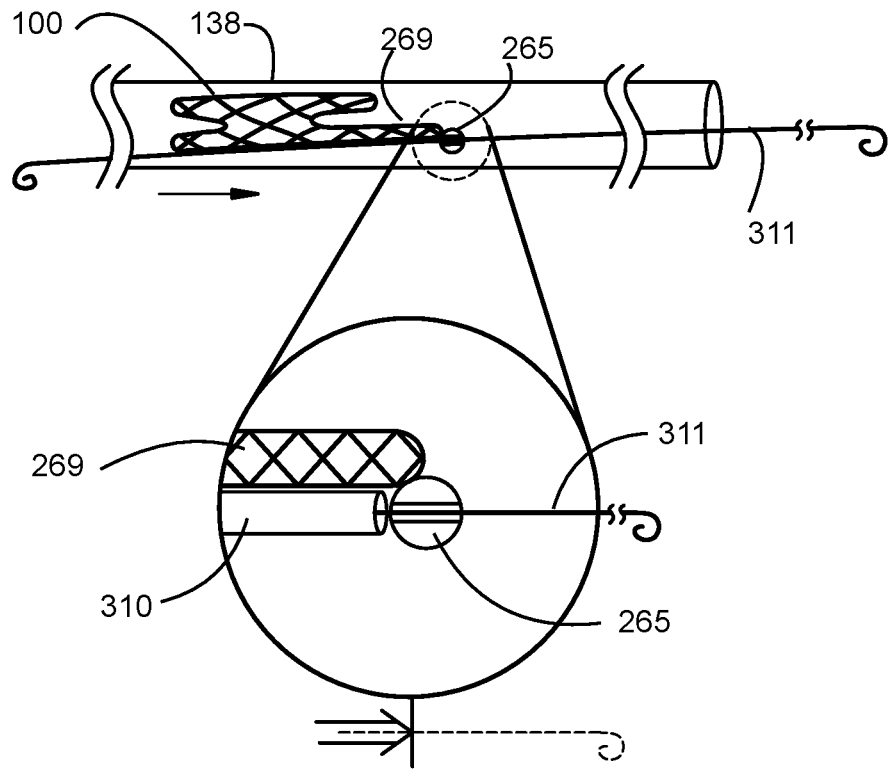

Referring now to the FIGURES, FIG. 1 is an illustration of a side or plan transparent view of a delivery catheter 138 loaded with a side-delivered (orthogonal) valve 100 having a tension arm 269 with a guidewire collar element 265 and a guidewire 311 extending through the guidewire collar 265 with a guidewire sheath 310 pushing against the guidewire collar element 265. Inset shows a non-limiting example of a guidewire collar 265 attached to a tension arm 269 with guidewire 311 through the aperture of the guidewire collar 265 and hypotube sheath 310 stopped by the larger circumference of the guidewire collar 265, permitting pushing on the tension arm 269 to pull the valve 100 out of the delivery catheter 138.

Figure 2:
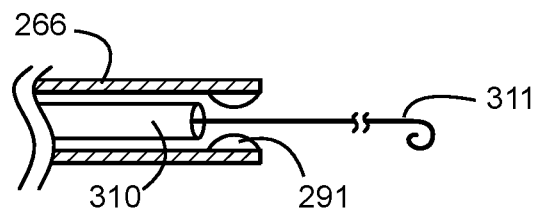
FIG. 2 is another non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

FIG. 2 is another non-limiting example of a guidewire collar 291 attached to a tension arm 269 with guidewire 311 through the aperture of the guidewire collar 291 and hypotube sheath 310 stopped by the larger circumference of the guidewire collar 291, permitting pushing on the tension arm 269 to pull the valve out of the delivery catheter 138.

Figure 3:
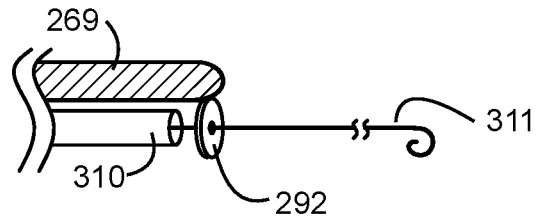
FIG. 3 is another non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

FIG. 3 is another non-limiting example of a guidewire collar 292 attached to a tension arm 269 with guidewire 311 through the aperture of the guidewire collar 292 and hypotube sheath 310 stopped, as it slides over the guidewire—the guidewire is in lumen of hypotube sheath—by the larger circumference of the guidewire collar 292, permitting pushing on the tension arm 269 to pull the valve out of the delivery catheter 138.

Figure 4:
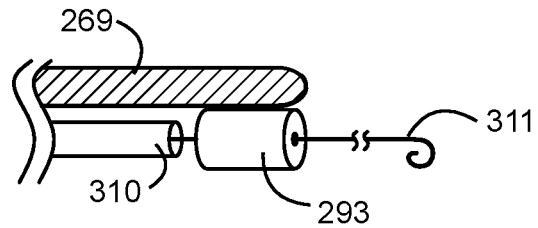
FIG. 4 is another non-limiting example of a guidewire collar attached to a tension arm with guidewire through the aperture of the guidewire collar and hypotube sheath stopped by the larger circumference of the guidewire collar, permitting pushing on the tension arm to pull the valve out of the delivery catheter.

FIG. 4 is another non-limiting example of a guidewire collar 293 attached to a tension arm 269 with guidewire 311 through the aperture of the guidewire collar 293 and hypotube sheath 310 stopped by the larger circumference of the guidewire collar 293, permitting pushing on the tension arm 269 to pull the valve out of the delivery catheter 138.

Figure 5:
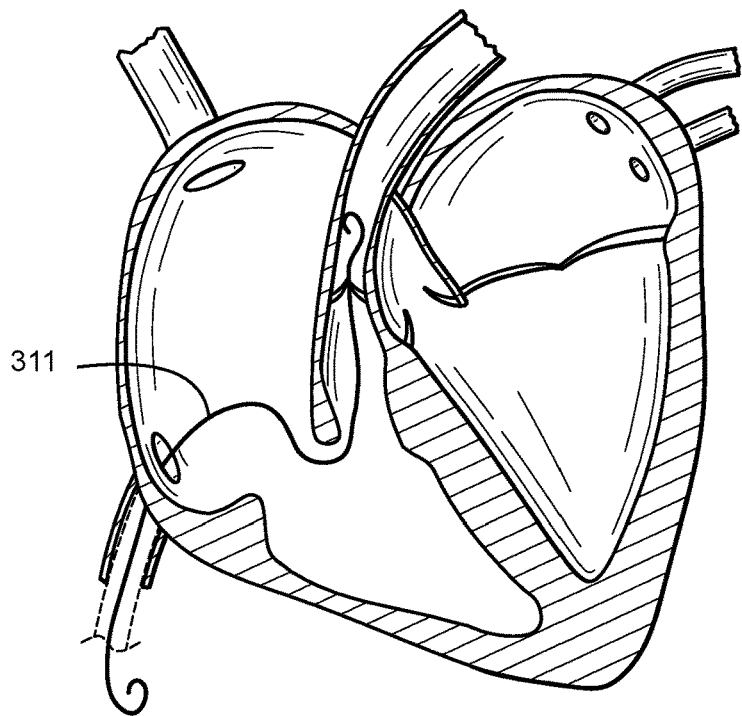
FIG. 5 is an illustration of step 1 of a 6-step process for delivery of an orthogonal prosthetic valve to the tricuspid annulus.

FIG. 5 is an illustration of step 1 of a 6-step process for delivery of an orthogonal prosthetic valve to the tricuspid annulus. FIG. 5 shows an 0.035 guidewire 311 with hypotube sheath delivered to the right ventricular outflow tract (RVOT).

Figure 6:
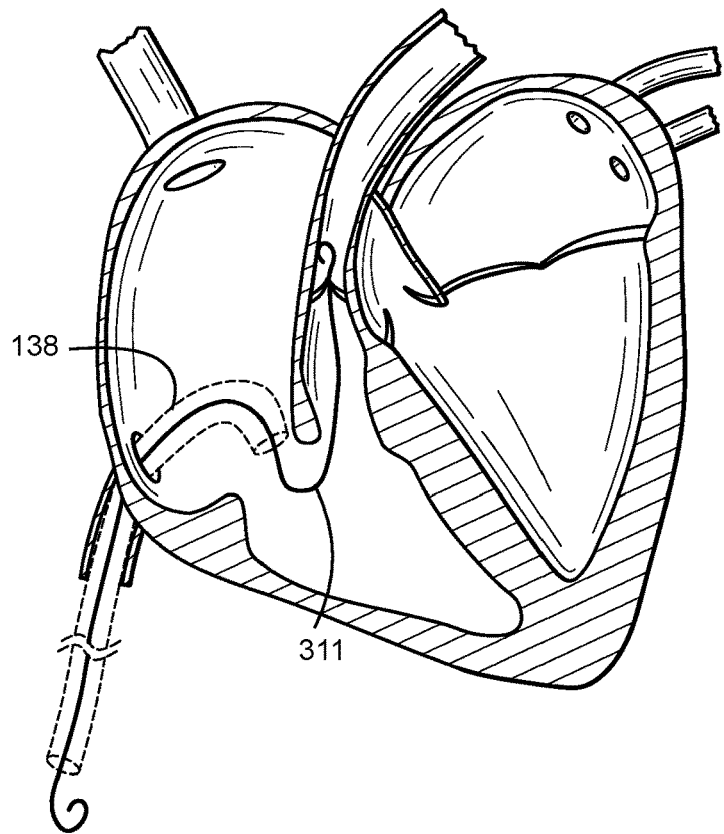
FIG. 6 is an illustration of step 2 of a 6-step process for delivery of an orthogonal prosthetic valve to the tricuspid annulus.

FIG. 6 is an illustration of step 2 of a 6-step process for delivery of an orthogonal prosthetic valve to the tricuspid annulus. FIG. 6 shows a 24-34 Fr delivery catheter 138 being advanced over the guidewire 311 to and through the native tricuspid annulus to the right ventricle.

FIG. 7 is an illustration of step 3 of a 6-step process for delivery of an orthogonal prosthetic valve to the tricuspid annulus. FIG. 7 shows a capsule/compression catheter 301 having a compressed valve 136 therein where the capsule 301 is loaded into the proximal end of the delivery catheter 138 and the valve is withdrawn from the capsule 301 into the delivery catheter 138, with sheathed guidewire 311 threaded through the valve and providing a wire path to the RVOT, planned deployment location.

FIG. 8 is an illustration of step 4 of a 6-step process for delivery of an orthogonal prosthetic valve to the tricuspid annulus. FIG. 8 shows the valve advanced up and out of the catheter 138 and deployed into the native annulus by pushing on the outer sheath 310 of the guidewire 311 to pull the valve 144 up the catheter and into position. Tension arm 269 is used to position the expanded valve 144.

FIG. 9 is an illustration of step 5 of a 6-step process for delivery of an orthogonal prosthetic valve to the tricuspid annulus. FIG. 9 shows a pushing catheter 310, or steerable catheter, being used to push the proximal side of the valve 144 into position within the annulus.

FIG. 10 is an illustration of step 6 of a 6-step process for delivery of an orthogonal prosthetic valve to the tricuspid annulus. FIG. 10 shows withdrawal of the delivery system and anchoring of the proximal side of the valve to the annular tissue. FIG. 10 shows expanded valve 144 with atrial sealing collar facing the atrium, valve body deployed within the native annulus and extending from atrium to ventricle, anchoring tension arm 269 is shown extending subannularly into the rvot area, and guidewire collar/ball 265 is shown at a distal end of the tension arm. Guide wire 311 and delivery catheter 138 are being withdrawn.

FIG. 11 is an illustration of step 1 of an 8-step process for delivery of an orthogonal prosthetic valve to the tricuspid annulus. FIG. 11 shows an 8 Fr guidewire 311 advanced from the femoral through the inferior vena cava (IVC) to the right atrium.

FIG. 12 is an illustration of step 2 of an 8-step process for delivery of an orthogonal prosthetic valve to the tricuspid annulus. FIG. 12 shows a balloon catheter 294 advanced over the guidewire 311 through the native annulus and into the RVOT to expand and push aside valve and leaflet tissue, chordae tendinae that might tangle transcatheter delivery of the valve.

FIG. 13 is an illustration of step 3 of an 8-step process for delivery of an orthogonal prosthetic valve to the tricuspid annulus. FIG. 13 shows an 0.035 guidewire 311 with hypotube sheath delivered to the right ventricular outflow tract (RVOT).

FIG. 14 is an illustration of step 4 of an 8-step process for delivery of an orthogonal prosthetic valve to the tricuspid annulus. FIG. 14 shows a 24-34 Fr delivery catheter 138 being advanced over the guidewire 311 to and through the native tricuspid annulus to the right ventricle.

FIG. 15 is an illustration of step 5 of an 8-step process for delivery of an orthogonal prosthetic valve 136 (compressed configuration) to the tricuspid annulus. FIG. 15 shows a capsule 301 having a compressed valve 136 therein where the capsule 301 or compression catheter is loaded into the proximal end of the delivery catheter 138 and the compressed valve 136 is advanced through the delivery catheter 138, with sheathed guidewire 311 threaded through the valve and providing a wire path to the RVOT, planned deployment location.

FIG. 16 is an illustration of step 6 of an 8-step process for delivery of an orthogonal prosthetic valve to the tricuspid annulus. FIG. 16 shows the expanded valve 144 advanced up the catheter, expelled, and deployed into the native annulus by pushing on the outer sheath (310) of the guidewire 311 to pull the valve, pulling from the guidewire collar at the distal end of the tension arm 269, up the catheter 138 and into position. Tension arm 269 is used to position the valve.

FIG. 17 is an illustration of step 7 of an 8-step process for delivery of an orthogonal prosthetic valve to the tricuspid annulus. FIG. 17 shows a hypotube sheath/guidewire 311, or steerable catheter, being used to push the proximal side (114) nearest the IVC or access point, of the valve 144 into position within the annulus.

FIG. 18 is an illustration of step 8 of an 8-step process for delivery of an orthogonal prosthetic valve to the tricuspid annulus. FIG. 18 shows withdrawal of the delivery system and anchoring of the proximal side of the valve 144 to the annular tissue and anchoring the distal side of the valve using the distal subannular anchoring tension arm 269.

FIG. 19 is an illustration of step 1 of a 6-step process for delivery of an orthogonal prosthetic valve to the tricuspid annulus. FIG. 19 shows the compressed side-deliverable valve 136 advanced up the catheter 138 using pushing sheath or rod 310 and deployed into the native annulus by following the track of the guidewire 311 which is disposed in the lumen of the pushing sheath 310.

FIG. 20 is an illustration of step 2 of a 6-step process for delivery of an orthogonal prosthetic valve to the tricuspid annulus. FIG. 20 shows pushing on the outer sheath 310 of the guidewire 311 tracking along with the guidewire 311 threaded through the guidewire collar 265 to pull the valve up the catheter 138 and into position, partially expelling the valve with tension arm 269 into the RVOT and the distal side of the valve lodged against the annular wall.

FIG. 21 is an illustration of step 3 of a 6-step process for delivery of an orthogonal prosthetic valve to the tricuspid annulus. FIG. 21 shows a pushing catheter 310 extending from the delivery catheter 138 being used to push the proximal side of the valve into position within the annulus.

FIG. 22 is an illustration of step 4 of a 6-step process for delivery of an orthogonal prosthetic valve to the tricuspid annulus. FIG. 22 shows how tension arm 269 is used to position the valve while pushing catheter 310 being used to push the proximal side of the valve into position within the annulus to allow the proximal subannular anchoring tab (proximal tab) 270 to engage and secure the valve against the native tissue.

FIG. 23 is an illustration of step 5 of a 6-step process for delivery of an orthogonal prosthetic valve to the tricuspid annulus. FIG. 23 shows how pushing catheter 310 delivers a tissue anchor 278 to secure the proximal side of the valve to the annular tissue.

FIG. 24 is an illustration of step 6 of a 6-step process for delivery of an orthogonal prosthetic valve to the tricuspid annulus. FIG. 24 shows withdrawal of the delivery system and anchoring of the proximal side of the valve to the annular tissue.

FIG. 25 is an illustration of step 1 of a 6-step process for delivery of a co-axial prosthetic valve to the tricuspid annulus.

FIG. 25 shows an 0.035 guidewire 311 with hypotube sheath delivered to the right ventricular outflow tract (RVOT) through the superior vena cava (SVC).

FIG. 26 is an illustration of step 2 of a 6-step process for delivery of a co-axial prosthetic valve to the tricuspid annulus.

FIG. 26 shows a 24-34 Fr delivery catheter 138 being advanced over the guidewire to and through the native tricuspid annulus to the right ventricle.

FIG. 27 is an illustration of step 3 of a 6-step process for delivery of a co-axial prosthetic valve to the tricuspid annulus. FIG. 27 shows a capsule 301 having a compressed valve 136 therein where the capsule 301 is loaded into the proximal end of the delivery catheter 138 and the valve is either withdrawn from the capsule 301 into the delivery catheter 138 for further advancement or capsule 301 is used to advance within the delivery catheter 138, with sheathed guidewire 311 threaded through the valve and providing a wire path to the RVOT, planned deployment location.

FIG. 28 is an illustration of step 4 of a 6-step process for delivery of a co-axial prosthetic valve to the tricuspid annulus. FIG. 28 shows the expanded valve 144 advanced up and expelled out of the catheter 138 and deployed into the native annulus by pushing on the outer sheath (310) of the guidewire 311 to pull the valve by the ball 265 up the catheter 138 and into position. Tension arm 269 is used as a ball 265 mount, to position the valve during deployment, and to provide subannular anchoring on the distal side.

FIG. 29 is an illustration of step 5 of a 6-step process for delivery of a co-axial prosthetic valve to the tricuspid annulus. FIG. 29 shows a pushing catheter 310 extending from the delivery catheter 138 being used to push the proximal side of the valve into position within the annulus.

FIG. 30 is an illustration of step 6 of a 6-step process for delivery of a co-axial prosthetic valve to the tricuspid annulus. FIG. 30 shows withdrawal of the delivery system and anchoring of the proximal side of the expanded valve 144 to the annular tissue.

FIG. 31 is an illustration of step 1 of a 4-step process for delivery of a co-axial prosthetic valve to the tricuspid annulus. FIG. 31 shows a co-axial compressed valve 136 being loaded using a compression capsule or compression catheter 301 into the distal end of the delivery catheter 138, with the sheathed 310 guidewire 311 threaded through the tension arm 269 and guidewire collar 291.

FIG. 32 is an illustration of step 2 of a 4-step process for delivery of a co-axial prosthetic valve to the tricuspid annulus. FIG. 32 shows a co-axial compressed valve 136 being delivered to the distal end of the delivery catheter 138, with the hypotube 310 sheathed guidewire 311 threaded through the tension arm 269 and channel-type guidewire collar 291.

FIG. 33 is an illustration of step 3 of a 4-step process for delivery of a co-axial prosthetic valve to the tricuspid annulus. FIG. 33 shows a co-axial compressed valve 136 partially expelled from the delivery catheter 138, with the tension arm 269 and channel-type guidewire collar 291 being positioned into the RVOT.

FIG. 34 is an illustration of step 4 of a 4-step process for delivery of a co-axial prosthetic valve to the tricuspid annulus. FIG. 34 shows that, once positioned, the self-expanding valve 144 can be completely expelled from the delivery catheter and deployed as a prosthetic valve.

FIG. 35 is an illustration of step 1 of a 7-step process for delivery of a co-axial prosthetic balloon-expandable valve to the tricuspid annulus. FIG. 35 shows an 0.035 guidewire 31 with hypotube sheath 310 delivered to the right ventricular outflow tract (RVOT) through the superior vena cava (SVC).

FIG. 36 is an illustration of step 2 of a 7-step process for delivery of a co-axial prosthetic valve to the tricuspid annulus. FIG. 36 shows a 24-34 Fr delivery catheter 138 being advanced over the guidewire 311/310 to and through the native tricuspid annulus to the right ventricle.

FIG. 37 is an illustration of step 3 of a 7-step process for delivery of a co-axial prosthetic valve to the tricuspid annulus. FIG. 37 shows a capsule 301 having a compressed valve 143 therein where the capsule 301 is loaded into the proximal end of the delivery catheter 138 and the valve is withdrawn/delivered from the capsule 301 into the delivery catheter 138, with sheathed guidewire 311 threaded through the valve and providing a wire path to the RVOT, planned deployment location.

FIG. 38 is an illustration of step 4 of a 7-step process for delivery of a co-axial prosthetic valve to the tricuspid annulus. FIG. 38 shows the valve 143 advanced up the catheter and deployed into the native annulus by pushing on the outer hypotube sheath 310 of the guidewire 311 to pull the valve 143 up the catheter 138 and into position. Tension arm 266 is used to position the valve.

FIG. 39 is an illustration of step 5 of a 7-step process for delivery of a co-axial prosthetic valve to the tricuspid annulus. FIG. 39 shows a steerable balloon catheter 295 being used to push the proximal side of the valve 143 into position within the annulus.

FIG. 40 is an illustration of step 6 of a 7-step process for delivery of a co-axial prosthetic valve to the tricuspid annulus. FIG. 40 shows balloon expansion of the co-axial valve 143 in the native annulus and anchoring of the proximal side of the valve to the annular tissue.

FIG. 41 is an illustration of step 7 of a 7-step process for delivery of a co-axial prosthetic valve to the tricuspid annulus. FIG. 41 shows withdrawal of the delivery system and anchoring of the proximal side of the expanded valve 143 to the annular tissue.

FIG. 42 is an illustration of step 1 of a 6-step process for delivery of a co-axial prosthetic valve to the tricuspid annulus. FIG. 42 shows the delivery catheter deployed to the native annulus.

FIG. 43 is an illustration of step 2 of a 6-step process for delivery of a co-axial prosthetic valve to the tricuspid annulus. FIG. 43 shows a co-axial balloon-expandable valve 143 being loaded into the delivery catheter 138, with the hypotube 310 sheathed guidewire 311 threaded through the tension arm 269 and channel-type guidewire collar 291.

FIG. 44 is an illustration of step 3 of a 6-step process for delivery of a co-axial balloon-expandable prosthetic valve 143 to the tricuspid annulus. FIG. 44 shows a co-axial valve 143 being delivered to the proximal end of the delivery catheter 138, with the hypotube 310 sheathed guidewire 311 threaded through the tension arm and guidewire collar 291.

FIG. 45 is an illustration of step 4 of a 6-step process for delivery of a co-axial prosthetic valve to the tricuspid annulus.

FIG. 45 shows a co-axial valve 143 partially expelled from the delivery catheter 138, with the tension arm and guidewire collar 291 being positioned into the RVOT. FIG. 45 shows balloon catheter 295 connected to the valve 143.

FIG. 46 is an illustration of step 5 of a 6-step process for delivery of a co-axial prosthetic valve to the tricuspid annulus. FIG. 46 shows that, once positioned and expanded by the balloon catheter 294, the balloon-expanded co-axial valve 143 can be completely deployed into the inner circumference of the native annulus to function as a prosthetic valve.

FIG. 47 is an illustration of step 6 of a 6-step process for delivery of a co-axial prosthetic valve 143 to the tricuspid annulus. FIG. 47 shows the deployed valve.

ADDITIONAL DEFINITIONS AND PARTS LIST

Below is provide a parts list in relation to claimed elements. Part numbering may refer to functional components and may be re-used across differing preferred embodiments to aid in uniformly understanding structure-function relationships. To avoid cluttering in drawing sheets, not every number may be added to the drawing sheets, or may be added later during examination as needed.

100 A dual-tab side delivered transcatheter prosthetic heart valve.
102 a self-expanding annular (outer) support frame.
103 Collar structure.
104 Central channel.
106 Outer perimeter wall.
107 Top edge of outer support frame.
108 Central vertical axis.
109 Z-axis, front to back, fold line axis.
110 Front wall portion of perimeter wall.
111 A2 clip
112 Back wall portion of perimeter wall.
113 A2 clip sleeve/pocket/sheath
114 Proximal side.
115 A2 clip steerable catheter/guidewire
116 Proximal fold area.
117 Secondary proximal fold areas.
118 Distal side.
119 A2 clip valve body attachment points
120 Distal fold area.
121 secondary distal fold areas.
122 Front upper collar portion.
128 Back lower body portion.
129 Sewn attachment points for inner to outer.
130 Flow control component, made of an inner frame having tissue leaflets mounted therein, collapsible (foldable and compressible), the inner mounted within the annular outer support frame and configured to permit blood flow in a first direction through an inflow end and block blood flow in the opposite, second direction, through the outflow end.
132 Inflow end.
134 Outflow end.
136 a compressed configuration
138 Delivery catheter. 21-33 Fr or 24-34 Fr
139 uncovered spacer
140 X-axis, a horizontal axis, parallel to delivery. catheter central axis
142 Intersecting angle 45-135 degrees, X-axis to Y-axis.
143 partially expanded, half-deployed valve
144 Expanded configuration.

146 Length-wise cylindrical axis of delivery catheter.
148 Height of about 5-60 mm.
150 Diameter of about 25-80 mm.
202 Plurality of compressible wire cells—outer frame.
204 Orientation and cell geometry substantially orthogonal to the central vertical axis to minimize wire cell strain when the annular support frame is compressed.
206 Vertical compressed configuration.
208 Folded configuration.
210 Folded and compressed configuration.
211 second A2 clip
212 Inner frame or outer frame shape selected from a funnel, cylinder, flat cone, or circular hyperboloid.
220 Braided matrix.
222 Wire frame matrix.
224 Laser-cut wire frame.
226 Biocompatible material.
227 Flared cuff on INNER frame.
228 Side profile of inner frame as a flat cone shape.
229 Non-cylindrical inner frame, e.g. elliptical section.
230 Diameter R of 40-80 mm.
231 INNER frame, for mounting leaflets.
232 Diameter r of 20-60 mm.
233 Set of uniform wire frame cells of INNER.
234 Height of 5-60 mm.
235 Non-uniform variable height cells of INNER.
236 Interior surface of annular outer support frame.
237 Non-uniform cell geometries, sizes in wire frame.
238 Exterior surface of annular outer support frame.
239 Compressed INNER.
240 Pericardial tissue for covering valve surfaces.
241 Diamond or eye-shaped wire cells.
242 Woven synthetic polyester material.
243 Eyelets on inner wire frame, consistent commissure attachment.
244 Outer support frame with an hourglass shape.
245 Laser cut attachment feature on inner frame.
246 Top diameter R1 of 40-80 mm.
248 Bottom diameter R2 of 50-70 mm.
250 Internal diameter r of 20-60 mm.
252 Height of 5-60 mm.
254 Internal diameter of 20-60 mm.
256 Height of 10-40 mm.
257 Leaflet band, mounting band for leaflet pockets.
258 LEAFLETS, plurality of leaflets, pericardial material.
259 Sewn edge of leaflet.
260 Rounded cylinder at an inflow end.
261 Open edge of leaflet
262 Flat closable aperture at an outflow end.
264 Longitudinal supports in/on flow control component, selected from rigid or semi-rigid posts, rigid or semi-rigid ribs, rigid or semi-rigid battons, rigid or semi-rigid panels, and combinations.
265 ball guide with eyelet
266 (any) Tab or tension arm extending from a distal side of the annular support frame.
268 DISTAL SUB-ANNULAR ANCHORING TAB, comprised of wire loop or wire frame, integrated frame section, or stent, extending from about 10-40 mm away from the annular support frame.
269 Independent Distal tab.
270 PROXIMAL anchoring tab
271 D-shape
272 Distal upper edge of the annular support frame.
273 Upper atrial tension arm, comprised of wire loop or wire frame extending from about 2-20 mm away from the annular support frame.
274 Lower tension arm comprised of wire loop or wire frame, integrated frame section, or stent, extending from about 10-40 mm away from the annular support frame.
276 Distal side of the annular support frame.
278 Tissue anchors connected to the annular support frame for engaging native tissue.
280 Front wall portion of frame is a first flat panel.
282 Back wall portion of frame is a second flat panel.
284 Sewn seam.
285 Hinge.
286 Flexible fabric span without any wire cells.
287 Fabric panel.
288 Braided-wire cells.
289 Commissure attachment—leaflet to frame.
290 Laser-cut wire cells.
291 wire guide channel-type
292 wire guide
293 wire guide
294 balloon catheter over guide wire
295 balloon catheter (any)
301 capsule delivery/compression catheter
302 Rolling into a compressed configuration.
304 Bilaterally rolling into a compressed configuration.
306 Flattening the annular support frame into two parallel panels that are substantially parallel to the long-axis.
308 Compressing the annular support frame along a vertical axis to reduce a vertical dimension of the valve from top to bottom.
310 Rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.
311 Guide wire.
312 Steerable catheter for rotating the heart valve prosthesis along an axis parallel to the plane of the valve annulus, wherein an upper tension arm mounted on the valve is conformationally pressure locked against supra-annular tissue, and wherein a lower tension arm mounted on the valve is conformationally pressure locked against sub-annular tissue.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A delivery system for deployment of a transcatheter prosthetic valve, comprising:
   (i) a hypotube sheathed guidewire assembly having an outer sheath and an inner guidewire shaft;
   (ii) a transcatheter prosthetic valve having an annular support frame with an atrial sealing collar, a flow control component mounted within the annular support frame, the annular support frame having a central axis, the flow control component is configured to permit blood flow in a first direction through an inflow end of the transcatheter prosthetic valve and block blood flow in a second direction, opposite the first direction, through an outflow end of the transcatheter prosthetic valve,
   a tension arm extends from a distal side of the annular support frame, the tension arm comprised of wire loop or wire frame, integrated frame section, or stent, extending from about 10-40 mm away from the annular support frame, said tension arm having a guidewire collar attached to the tension arm, wherein the guidewire collar is sized and configured with a guidewire aperture to allow the inner guidewire shaft to pass through the guidewire aperture, and to block passage of the outer sheath of the guidewire assembly through the guidewire aperture;
   (iii) a delivery catheter, the delivery catheter comprising an elongated tube with a central lumen, the lumen having a diameter from about 7 to 12 mm, the delivery catheter has a length-wise cylindrical axis substantially perpendicular to the central axis of the annular support frame of the transcatheter prosthetic valve when the transcatheter prosthetic valve is disposed within the delivery catheter;
   wherein the transcatheter prosthetic valve is compressible to a compressed configuration for introduction into the body using the delivery catheter for implanting at a desired location in the body,
   wherein the tension arm exits a distal end of the delivery catheter before the annular support frame,
   wherein the transcatheter prosthetic valve is expandable to an expanded configuration having a height of about 5-60 mm and a diameter of about 25-80 mm,
   wherein the compressed configuration of the transcatheter prosthetic valve has a compressed height configured to fit within the central lumen of the delivery catheter, a folded width configured to fit within the central lumen of the delivery catheter, and a length that is uncompressed along a long axis,
   wherein in said compressed configuration the long axis is oriented at an intersecting angle of between 45-135 degrees to the first direction, and in said expanded configuration the long axis is oriented at an intersecting angle of between 45-135 degrees to the first direction,
   wherein the long axis of the compressed configuration of the valve is substantially parallel to the length-wise cylindrical axis of the delivery catheter when the transcatheter prosthetic valve is disposed within the delivery catheter.

2. The system of claim 1, wherein the transcatheter prosthetic valve is an atrioventricular valve.

3. The system of claim 1, wherein the annular support frame comprises a plurality of superelastic compressible wire cells, wherein said frame is covered with pericardial tissue, and said frame is partially or completely covered with a polyester outer covering.

4. The system of claim 1, wherein the guidewire is disposed within a lumen of the sheath, and an outer diameter of the sheath is larger than the guidewire collar aperture, wherein the sheath is configured as a pusher to advance the sheath over the guidewire to push on the guidewire collar and advance the valve within the delivery catheter and to the desired location within a patient.

5. The system of claim 1, wherein the annular support frame has a ventricular sealing collar.

6. A delivery system for deployment of a transcatheter prosthetic valve, comprising:
   a valve frame having a central axis and defining an aperture extending along the central axis;
   wherein the valve frame has an expanded configuration with a first height along the central axis, a first lateral width along a lateral axis perpendicular to the central axis, and a first longitudinal length along a longitudinal axis perpendicular to the central axis and the lateral axis, and the frame has a compressed configuration with a second height, less than the first height, along the central axis and a second lateral width, less than the first lateral width, along the lateral axis;
   a guidewire collar having an aperture configured to thread a guidewire through the aperture;
   a flow control component mounted within the aperture of the valve frame and configured to permit blood flow in a first direction approximately parallel to the central axis from an inflow end to an outflow end of the flow control component and block blood flow in a second direction, opposite the first direction;
   a delivery catheter having a lumen, the lumen having a diameter less than the first height of the valve frame, less than the first lateral width of the valve frame, greater than the second height of the valve frame, and greater than the second lateral width of the valve frame, the delivery catheter having a cylindrical axis substantially perpendicular to the central axis of the valve frame when the transcatheter prosthetic valve is disposed within the delivery catheter;
   wherein the valve frame includes a tension arm extending from a distal side of the valve frame; and the guidewire collar is disposed on the tension arm; and
   a pusher sheath having a distal end and a diameter larger than the internal diameter of the aperture of the guidewire collar, the pusher sheath disposable over the guidewire, said pusher sheath having a distal end configured to engage with the guidewire collar to push transcatheter prosthetic valve from the compressed configuration when the transcatheter prosthetic valve is disposed in the lumen of the delivery catheter to the expanded configuration;
   wherein the valve is compressible to the compressed configuration for sideways delivery into the body using the delivery catheter for implanting at a desired location in a patient, and
   wherein the tension arm is configured to exit a distal end of the delivery catheter before the annular support frame when the transcatheter prosthetic valve is expelled from the delivery catheter.

7. The system of claim 6, wherein the transcatheter prosthetic valve is an atrioventricular valve.

8. The system of claim 6, wherein the valve frame comprises a plurality of superelastic compressible wire cells, wherein said valve frame is covered with pericardial tissue, and said frame is partially or completely covered with a polyester outer covering.

9. The system of claim 6, wherein the valve frame has an upper atrial sealing collar attached to an upper edge of the valve frame.

10. The system of claim 6, wherein the valve frame has a lower ventricular sealing collar attached to a lower edge of the valve frame.

\* \* \* \* \*